United States Patent
Sekiguchi et al.

(10) Patent No.: US 9,382,426 B2
(45) Date of Patent: Jul. 5, 2016

(54) WATER-INSOLUBLE COLORING COMPOUND, INK, THERMAL TRANSFER RECORDING SHEET, AND COLOR FILTER RESIST COMPOSITION

(71) Applicant: CANON KABUSHIKI KAISHA, Tokyo (JP)

(72) Inventors: Takeshi Sekiguchi, Tokyo (JP); Shosei Mori, Hiratsuka (JP); Taichi Shintou, Saitama (JP); Yuko Katsumoto, Yokohama (JP); Takayuki Ujifusa, Ashigarakami-gun (JP); Takeshi Miyazaki, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/373,327

(22) PCT Filed: Jan. 16, 2013

(86) PCT No.: PCT/JP2013/051228
§ 371 (c)(1),
(2) Date: Jul. 18, 2014

(87) PCT Pub. No.: WO2013/108925
PCT Pub. Date: Jul. 25, 2013

(65) Prior Publication Data
US 2014/0370207 A1 Dec. 18, 2014

(30) Foreign Application Priority Data
Jan. 20, 2012 (JP) .................................. 2012-010325

(51) Int. Cl.
| | | |
|---|---|---|
| C09D 11/037 | (2014.01) | |
| C09D 11/322 | (2014.01) | |
| C09B 29/42 | (2006.01) | |
| C07D 213/80 | (2006.01) | |
| C07D 213/82 | (2006.01) | |
| C07D 213/89 | (2006.01) | |
| B41M 5/388 | (2006.01) | |
| G02B 5/22 | (2006.01) | |
| G03F 3/00 | (2006.01) | |
| C09B 29/01 | (2006.01) | |

(52) U.S. Cl.
CPC ............ *C09B 29/3639* (2013.01); *B41M 5/388* (2013.01); *C07D 213/89* (2013.01); *C09B 29/0003* (2013.01); *C09B 29/0007* (2013.01); *C09B 29/3626* (2013.01); *C09D 11/037* (2013.01); *C09D 11/322* (2013.01); *G02B 5/223* (2013.01)

(58) Field of Classification Search
CPC .. C09D 11/037; C09D 11/322; C09B 29/003; C09B 29/007; C09B 29/363; C07D 213/80; C07D 213/82; C07D 213/89; B41M 5/388; G02B 5/223; G03F 7/0007
USPC ........................ 106/31.48; 534/772; 428/32.6
See application file for complete search history.

(56) References Cited

U.S. PATENT DOCUMENTS

| | | | | |
|---|---|---|---|---|
| 4,140,684 A * | 2/1979 | Burkhard | ............. | C07D 213/80 534/772 |
| 7,193,068 B2 * | 3/2007 | Araki | .................. | C07D 213/85 534/772 |
| 7,504,488 B2 * | 3/2009 | Toyoda | ............... | C09B 29/0007 106/31.48 |
| 7,833,685 B2 * | 11/2010 | Tanaka | ................ | C09B 29/0003 534/772 |
| 8,211,221 B2 * | 7/2012 | Tanaka | ................ | C09D 11/328 106/31.48 |
| 8,211,606 B2 * | 7/2012 | Murai | .................... | B41M 5/388 106/31.47 |
| 2009/0075193 A1 * | 3/2009 | Murai | .................... | B41M 5/388 534/772 |
| 2009/0202934 A1 | 8/2009 | Hasegawa | | |
| 2010/0035171 A1 * | 2/2010 | Watanabe | ............. | C09B 29/363 430/108.23 |
| 2010/0248112 A1 | 9/2010 | Fukushima et al. | | |
| 2014/0170553 A1 * | 6/2014 | Mori | ...................... | G03G 9/122 430/108.23 |
| 2015/0010865 A1 * | 1/2015 | Mori | ..................... | G03F 7/0007 430/281.1 |
| 2015/0140487 A1 * | 5/2015 | Sekiguchi | ............ | G03G 9/0806 430/108.23 |

FOREIGN PATENT DOCUMENTS

| | | |
|---|---|---|
| DE | 1901711 A1 | 4/1970 |
| GB | 1360749 | 7/1974 |
| JP | 61-112160 A | 5/1986 |
| JP | H07-140716 A | 6/1995 |
| JP | H08-034933 A | 2/1996 |
| JP | H11-282208 A | 10/1999 |
| JP | 2000-062327 A | 2/2000 |
| JP | 2004-300225 A | 10/2004 |
| JP | 2006-124634 A | 5/2006 |
| JP | 2011-257706 A | 12/2011 |
| WO | 2008/114886 A1 | 9/2008 |
| WO | 2009/088034 A1 | 7/2009 |
| WO | 2012/026607 A1 | 3/2012 |

* cited by examiner

*Primary Examiner* — Helene Klemanski
(74) *Attorney, Agent, or Firm* — Canon U.S.A., Inc., IP Division

(57) ABSTRACT

The present invention provides a water-insoluble coloring compound having excellent light resistance, an ink containing the coloring compound, a thermal transfer recording sheet including a coloring material layer formed on a base material from the ink, and a color filter resist composition containing the ink.

5 Claims, 1 Drawing Sheet

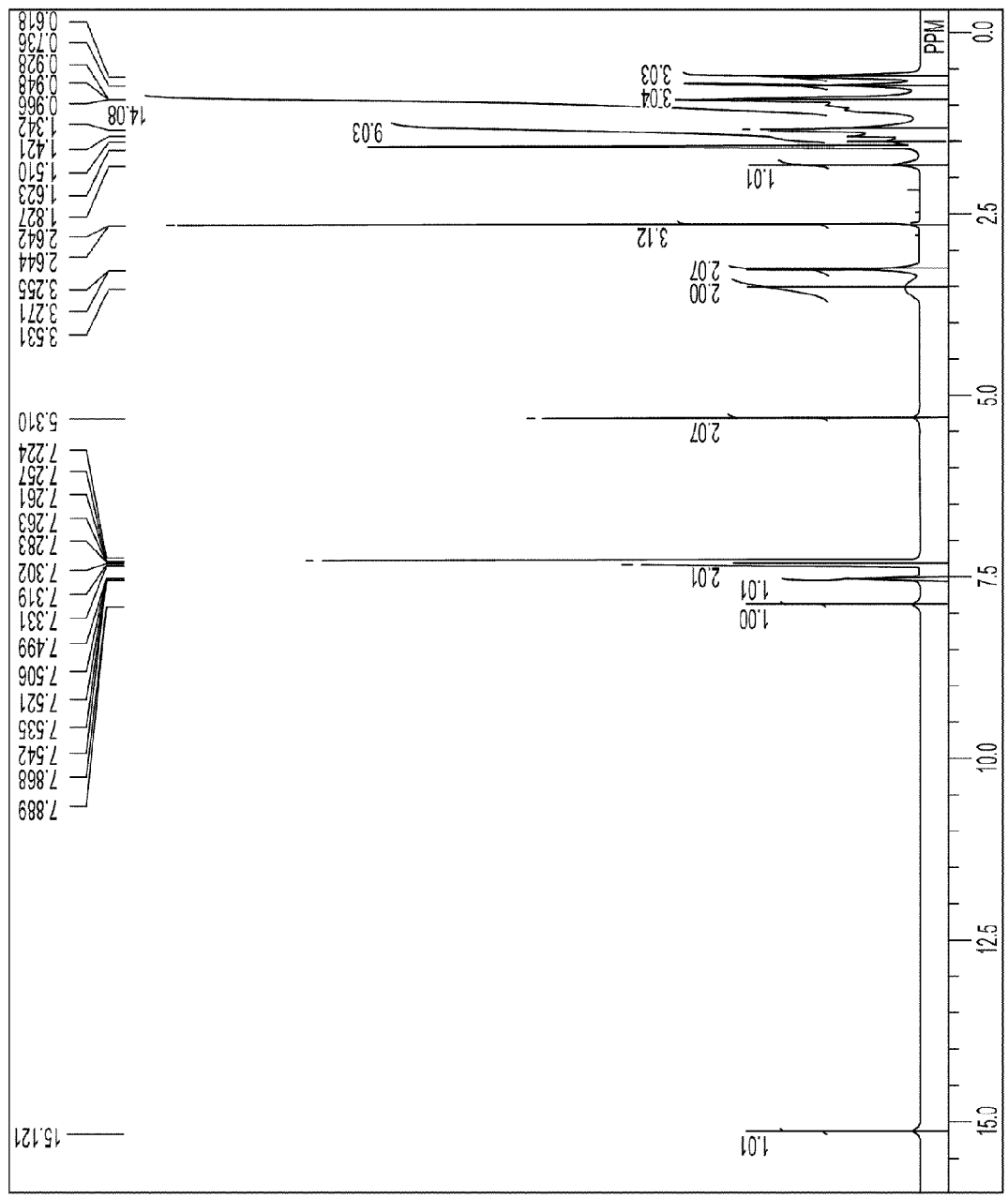

WATER-INSOLUBLE COLORING COMPOUND, INK, THERMAL TRANSFER RECORDING SHEET, AND COLOR FILTER RESIST COMPOSITION

TECHNICAL FIELD

The present invention relates to a water-insoluble coloring compound and relates to an ink, a thermal transfer recording sheet, and a color filter resist composition each containing the water-insoluble coloring compound.

BACKGROUND ART

Recently, higher image quality has been demanded in color images including color liquid crystal displays. A color filter is indispensable for color display of a liquid crystal display and is an important component that determines the performance of a liquid crystal display. Color filters can be produced by a known method such as a dyeing method, a printing method, an ink-jet method, or a photo-resist method. In particular, the photo-resist method can easily control the spectral characteristics and color reproducibility and allows highly fine patterning because of its high resolution and is therefore a main method for producing color filters.

In the photo-resist method, the coloring agents are generally pigments. However, the pigment has a certain particle size distribution and is thereby accompanied by a depolarization effect (collapse of polarization) to reduce the contrast ratio of color display of a liquid crystal display when the pigment contains particles having large particle diameters. Additionally, in a liquid crystal display using a pigment, since the pigment prevents the transmission of backlight, it is difficult to enhance the brightness of a color filter. Furthermore, the pigment is insoluble in organic solvents and polymers and is therefore present as a dispersion in a color resist composition. Unfortunately, the stabilization of the dispersion is difficult.

In contrast, many dyes are generally soluble in organic solvents and polymers, and an appropriately selected dye can be stabilized without occurrence of aggregation even in a color resist composition. Accordingly, in a color filter produced from a resist composition containing a dye as the coloring agent, the dye is dispersed in a molecular level. As a result, the depolarization effect hardly occurs, and high transmission of backlight is provided.

The use of a yellow color filter containing a monoazo dye as a coloring agent has been proposed until now for enabling an image to be displayed with satisfactory spectral characteristics and high contrast (see Patent Literature 1). However, in order to display a finer image, it is necessary to develop a color filter having higher light resistance and better spectral characteristics and achieving a higher contrast ratio.

Furthermore, there are demands for improvement of coloring compounds in other fields than color filters.

One of such demands is an image-forming method employing thermal transfer recording. The thermal transfer recording forms an image by stacking a thermal transfer sheet having a coloring material layer containing a heat-transferable coloring material and an image-receiving sheet having a surface provided with a coloring material-receiving layer on a sheet-like base material and heating the thermal transfer sheet to transfer the coloring material in the thermal transfer sheet to the image-receiving sheet and thereby to perform the recording. In the thermal transfer recording, the coloring compounds contained in the transfer sheet and in the ink composition for the transfer sheet highly affect the transfer recording speed and the quality and storage stability of the recorded matter and are therefore very important materials. As the dyes used in such thermal transfer recording, methine disperse dyes such as C.I. Disperse Yellow 201, disazo disperse dyes such as C.I. Disperse Orange 13, and pyridone azo disperse dyes have been proposed (see Patent Literature 2). However, there is even now a demand for developing a coloring compound having further enhanced light resistance.

CITATION LIST

Patent Literature

PTL 1 Japanese Patent Laid-Open No. 2006-124634
PTL 2 Japanese Patent Laid-Open No. 2000-062327

SUMMARY OF INVENTION

The present invention provides a water-insoluble coloring compound having excellent light resistance.

The present invention also provides an ink, a thermal transfer recording sheet, and a color filter resist composition each having excellent light resistance.

The above-described problems are solved by using the following water-insoluble coloring compound.

The present invention relates to a water-insoluble coloring compound having a structure represented by Formula (1):

[Chem. 1]

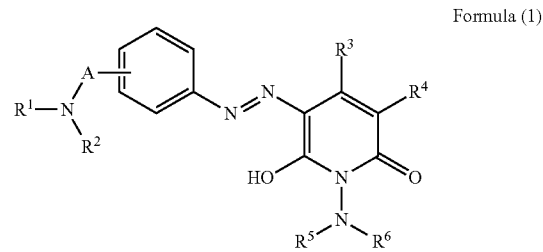

Formula (1)

(in Formula (1), $R^1$ and $R^2$ each independently represent a hydrogen atom or an alkyl group; $R^3$ represents an alkyl group, an aryl group, or an amino group; $R^4$ represents a hydrogen atom, a cyano group, a carbamoyl group, a carboxylic acid ester group, or a carboxylic acid amide group; $R^5$ and $R^6$ each independently represent a hydrogen atom, an alkyl group, or an acyl group or $R^5$ and $R^6$ bind to each other to form a ring; and A represents a carbonyl group or a sulfonyl group).

The present invention also relates to an ink containing the water-insoluble coloring compound.

The present invention also relates to a thermal transfer recording sheet composed of a base material and a coloring material layer formed on the base material from a composition containing the water-insoluble coloring compound.

The present invention also relates to a color filter resist composition containing the water-insoluble coloring compound.

ADVANTAGEOUS EFFECTS OF INVENTION

The present invention can provide a water-insoluble coloring compound having excellent light resistance. Furthermore, the present invention can provide an ink, a thermal transfer recording sheet, and a color filter resist composition each having excellent light resistance.

BRIEF DESCRIPTION OF DRAWING

FIG. 1 is a $^1$H-NMR spectrum of Compound (1), which is one of water-insoluble coloring compounds having a structure represented by Formula (1) of the present invention, in $CDCl_3$ at room temperature at 400 MHz.

DESCRIPTION OF EMBODIMENTS

The present invention will now be described in more detail.

The present inventors have diligently studied for solving the above-mentioned problems and, as a result, have found that a water-insoluble coloring compound having a structure represented by Formula (1) has excellent light resistance,

[Chem. 2]

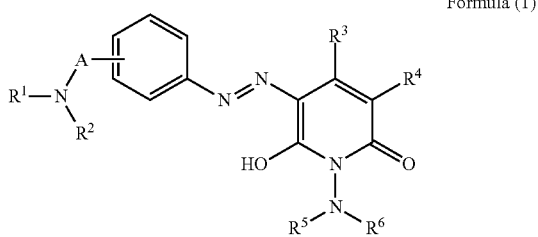

Formula (1)

(in Formula (1), $R^1$ and $R^2$ each independently represent a hydrogen atom or an alkyl group; $R^3$ represents an alkyl group, an aryl group, or an amino group; $R^4$ represents a hydrogen atom, a cyano group, a carbamoyl group, a carboxylic acid ester group, or a carboxylic acid amide group; $R^5$ and $R^6$ each independently represent a hydrogen atom, an alkyl group, or an acyl group or $R^5$ and $R^6$ bind to each other to form a ring; and A represents a carbonyl group or a sulfonyl group).

The inventors have also found that an ink, a thermal transfer recording sheet, and a color filter resist composition each having excellent light resistance can be provided by using the water-insoluble coloring compound and have accomplished the present invention.

The water-insoluble coloring compound having a structure represented by Formula (1) will now be described.

The water-insoluble coloring compound represented by Formula (1) of the present invention has high affinity to organic solvents. In the present invention, the term "water-insoluble" refers to that the solubility in water is less than 1% by mass.

In Formula (1), examples of the alkyl group represented by $R_1$ or $R_2$ include, but are not limited to, saturated or unsaturated, linear, branched, or cyclic, and primary, secondary, or tertiary C1-20 alkyl groups such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methyl cyclohexyl group, a 2-ethylpropyl group, a 2-ethylhexyl group, and a cyclohexenyl ethyl group.

Among these groups, $R^1$ and $R^2$ can be each independently an ethyl group, a n-butyl group, a sec-butyl group, a dodecyl group, a cyclohexyl group, a methyl cyclohexyl group, a 2-ethylpropyl group, a 2-ethylhexyl group, or a cyclohexenyl ethyl group, in particular, a n-butyl group or a 2-ethylhexyl group, for providing excellent light resistance. Furthermore, $R^1$ and $R^2$ can be the same alkyl group for providing excellent light resistance.

In Formula (1), examples of the alkyl group represented by $R^3$ include, but are not limited to, a methyl group, an ethyl group, a propyl group, and a butyl group.

Examples of the aryl group represented by $R^3$ include, but are not limited to, a phenyl group.

Examples of the amino group represented by $R^3$ include, but are not limited to, an amino group and a dimethylamino group.

Among these groups, $R^3$ can be an alkyl group, in particular, a methyl group, for providing excellent light resistance.

In Formula (1), examples of the carboxylic acid ester group represented by $R^4$ include, but are not limited to, a carboxylic acid methyl ester group and a carboxylic acid ethyl ester group.

In Formula (1), examples of the carboxylic acid amide group represented by $R^4$ include, but are not limited to, carboxylic acid dialkylamide groups such as a carboxylic acid dimethyl amide group and a carboxylic acid diethylamide group and carboxylic acid monoalkylamide groups such as a carboxylic acid methylamide group and a carboxylic acid ethylamide group.

In Formula (1), $R^4$ represents a hydrogen atom, a cyano group, a carbamoyl group, a carboxylic acid ester group, or a carboxylic acid amide group, as described above. Among these groups, $R^4$ can be a cyano group for providing excellent light resistance.

In Formula (1), examples of the alkyl group represented by $R^5$ or $R^6$ include, but are not limited to, saturated or unsaturated, linear, branched, or cyclic, and primary, secondary, or tertiary C1-20 alkyl groups such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methyl cyclohexyl group, a 2-ethylpropyl group, a 2-ethylhexyl group, and a cyclohexenyl ethyl group.

In Formula (1), examples of the acyl group represented by $R^5$ or $R^6$ include, but are not limited to, a formyl group, an acetyl group, an ethylhexynoyl group, and a benzoyl group. In particular, $R^5$ and $R^6$ can be each independently a methyl group, a butyl group, an ethylhexynoyl group, or a benzoyl group for providing excellent light resistance.

In Formula (1), the ring formed by binding of $R^5$ and $R^6$ is not limited as long as the ring does not affect the light resistance. Examples of the ring include a pyrrolidine ring, a piperidine ring, an azepane ring, and an azocane ring.

In Formula (1), A represents a carbonyl group or a sulfonyl group, as described above. Among these groups, A can be a carbonyl group for providing excellent light resistance.

Incidentally, though Formula (1) shows an azo form, a tautomer of the structure represented by Formula (1), the hydrazo form, may be present together with the azo form.

The water-insoluble coloring compound having a structure represented by Formula (1) according to the present invention can be synthesized in accordance with the known method described in WO08/114886.

An embodiment of the method of producing the water-insoluble coloring compound having a structure represented by Formula (1) of the present invention is shown below, but the method is not limited thereto.

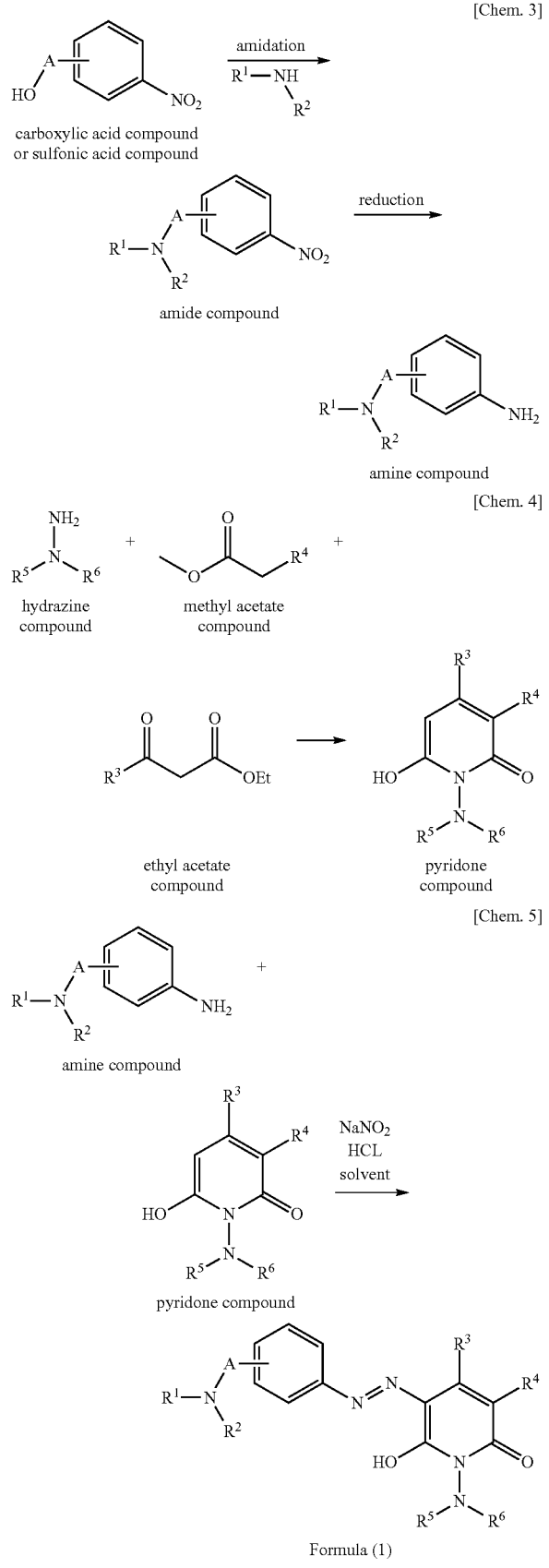

$R^1$ to $R^6$ and A in each compound in the reaction formulae and in the compound having a structure represented by Formula (1) are each independently synonymous with $R^1$ to $R^6$ and A in the above-mentioned Formula (1).

The water-insoluble coloring compound of the present invention can be produced by coupling of an amine compound and a pyridone compound.

A method of producing the amine compound will be described.

The amine compound can be synthesized by preparing an amide compound through amidation of the carboxylic acid compound or the sulfonic acid compound and reducing the amide compound.

The carboxylic acid compound or the sulfonic acid compound used in the present invention and the amine compound used in the amidation process are commercially available and are therefore easily available.

The amidation process will now be described.

The amidation process may be performed in the absence of a solvent, but is particularly performed in the presence of a solvent. Any solvent that does not participate in the reaction can be used, and examples of the solvent include chloroform, dichloromethane, N,N-dimethylformamide, toluene, xylene, tetrahydrofuran, dioxane, acetonitrile, and ethyl acetate. In addition, a mixture of two or more solvents can be used, and the mixing ratio of the solvents can be appropriately determined. The amount of the reaction solvent used can be 0.1 to 1000 times, such as 1.0 to 150 times, the amount of the carboxylic acid compound or the sulfonic acid compound.

The reaction temperature of the amidation process can be in the range of $-80°$ C. to $250°$ C., such as $-20°$ C. to $150°$ C. The amidation reaction is usually completed within 24 hours.

The use of a chlorinating agent such as thionyl chloride or oxalyl chloride facilitates the amidation. There are many commercially available chlorinating agents. Among such chlorinating agents, thionyl chloride is inexpensively available and is easy to handle. The amount of the thionyl chloride used can be 0.1 to 10 times, such as 0.5 to 5.0 times, and even 0.8 to 2.0 times, the amount of the carboxylic acid compound or the sulfonic acid compound.

Furthermore, the use of a catalyst such as diethylamine, pyridine, or dimethylaminopyridine facilitates the reaction.

After the completion of the reaction, purification such as distillation, recrystallization, or silica gel chromatography is performed to yield a desired amide compound. Subsequently, the reduction process is performed, which will now be described.

The reduction process may be performed in the absence of a solvent, but is particularly performed in the presence of a solvent. Any solvent that does not participate in the reaction can be used, and examples of the solvent include water, methanol, ethanol, tetrahydrofuran, N,N-dimethylformamide, dichloromethane, dioxane, ethyl acetate, toluene, and acetonitrile. In addition, a mixture of two or more solvents can be used, and the mixing ratio of the solvents can be appropriately determined. The amount of the reaction solvent used can be 0.1 to 1000 times, such as 1.0 to 150 times, the amount of the amide compound.

Furthermore, the use of a catalyst such as palladium on carbon facilitates the reduction. A reducing agent such as hydrogen, ammonium formate, or hydrazine can be used.

The reduction process may be performed under an ordinary pressure or under increased pressure with an apparatus such as an autoclave.

After the completion of the reaction, purification such as distillation, recrystallization, or silica gel chromatography is performed to yield a desired amine compound.

A method of producing the pyridone compound will now be described.

The pyridone compound can be synthesized by a three-component coupling reaction of a hydrazine compound, a methyl acetate compound, and an ethyl acetate compound.

The reduction process may be performed in the absence of a solvent, but is particularly performed in the presence of a solvent. Any solvent that does not participate in the reaction can be used, and examples of the solvent include water, methanol, ethanol, acetic acid, and toluene. In addition, a mixture of two or more solvents can be used, and the mixing ratio of the solvents can be appropriately determined. The amount of the reaction solvent used can be 0.1 to 1000 times, such as 1.0 to 150 times, the amount of the methyl acetate compound.

Furthermore, the use of a base facilitates the reduction. Specific examples of the usable base include organic bases such as pyridine, 2-methylpyridine, diethylamine, diisopropylamine, triethylamine, phenylethylamine, isopropylethylamine, methylaniline, 1,4-diazabicyclo[2.2.2]octane (DABCO), tetrabutylammonium hydroxide, 1,8-diazabicyclo[5.4.0]undecene (DBU), and potassium acetate; organic metals such as n-butyllithium and tert-butyl magnesium chloride; inorganic bases such as sodium borohydride, metallic sodium, potassium hydride, and calcium oxide; and metal alkoxides such as potassium tert-butoxide, sodium tert-butoxide, and sodium ethoxide. Among these bases, in particular, triethylamine or piperidine, further triethylamine, can be used. The amount of the base used can be 0.1 to 20 times, such as 0.8 to 10 times, and even 0.9 to 2.0 times, the amount of the methyl acetate compound.

After the completion of the reaction, purification such as distillation, recrystallization, or silica gel chromatography is performed to yield a desired pyridone compound.

A process of forming a coloring compound by coupling of the amine compound and the pyridone compound will now be described.

The coloring compound can be formed by a known method. That is, the water-insoluble coloring compound having a structure represented by Formula (1) of the present invention can be prepared by coupling of the pyridone compound and a diazo component derived from the amine compound.

A specific example of the coupling will now be described.

The amine compound is reacted with a nitrite such as sodium nitrite in a water solvent in the presence of an inorganic acid such as hydrochloric acid or sulfuric acid to be converted into the corresponding diazonium salt. The diazonium salt is subjected to coupling with the pyridone compound to produce a water-insoluble coloring compound having a structure represented by Formula (1).

The resulting water-insoluble coloring compound having a structure represented by Formula (1) is subjected to after-treatment that is usually performed in organic synthesis and then to purification, such as liquid separation, recrystallization, reprecipitation, or column chromatography, to yield a highly purified water-insoluble coloring compound. The resulting water-insoluble coloring compound having a structure represented by Formula (1) can be identified using a $^1$H nuclear magnetic resonance ($^1$H-NMR) spectrometer and a matrix-assisted laser desorption-ionization mass spectrometer (MALDI-TOF-MS).

The water-insoluble coloring compounds each having a structure represented by Formula (1) of the present invention may be used alone or in combination for controlling, for example, the color tone according to the purpose of the use. Furthermore, the water-insoluble coloring compound can be used in combination with one or more known pigments or dyes.

As nonlimiting examples of the water-insoluble coloring compound of the present invention, the following Compounds (1) to (33) are shown. In particular, Compounds (1), (2), (4), (5), (6), (8), (11), (13), (14), (15), (28), (30), (31), and (33) are excellent.

[Chem. 6]

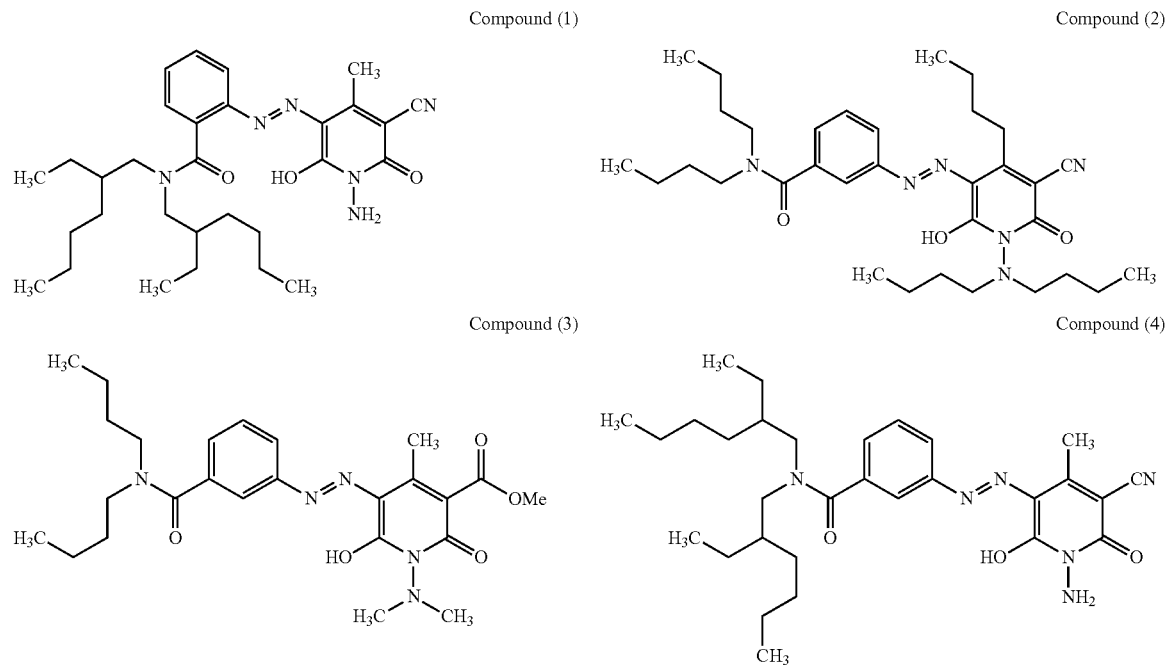

-continued
Compound (5)
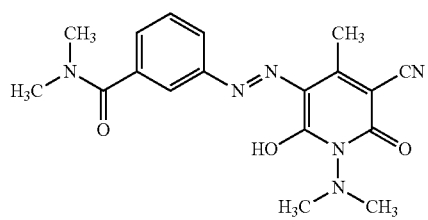
Compound (6)
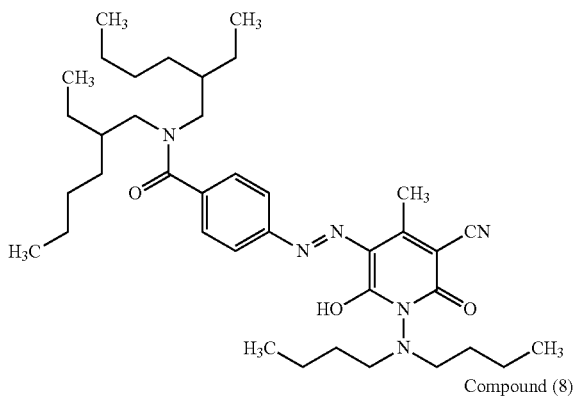
Compound (7)
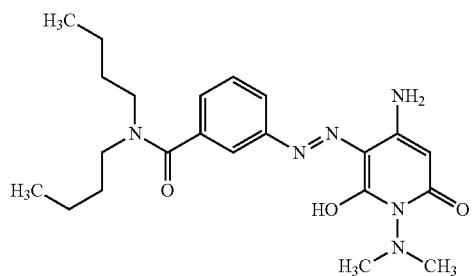
Compound (8)
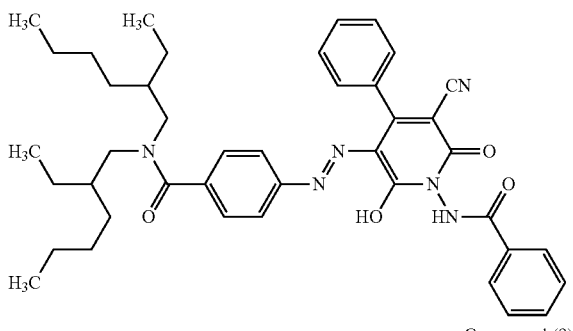
Compound (9)
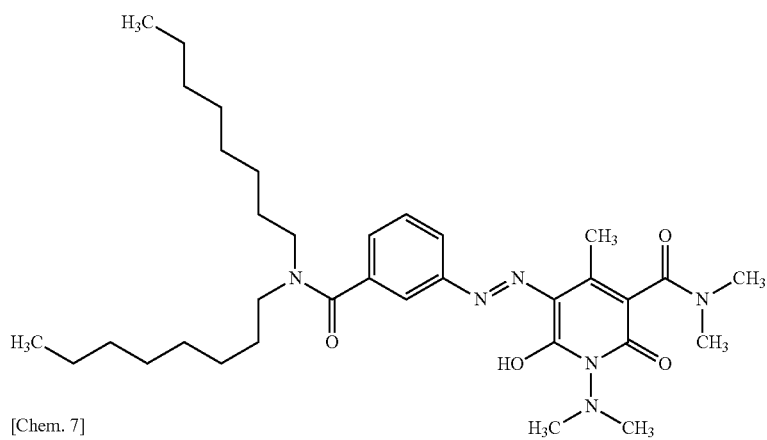
[Chem. 7]
Compound (10)
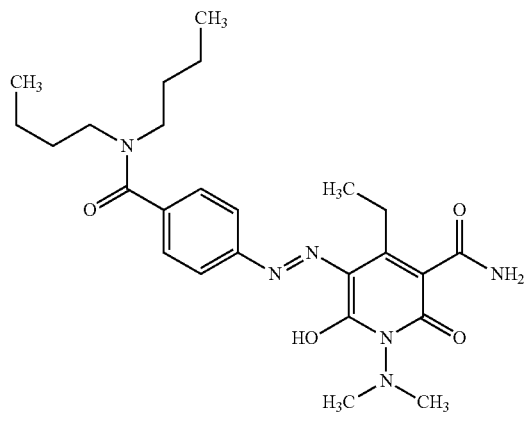
Compound (11)
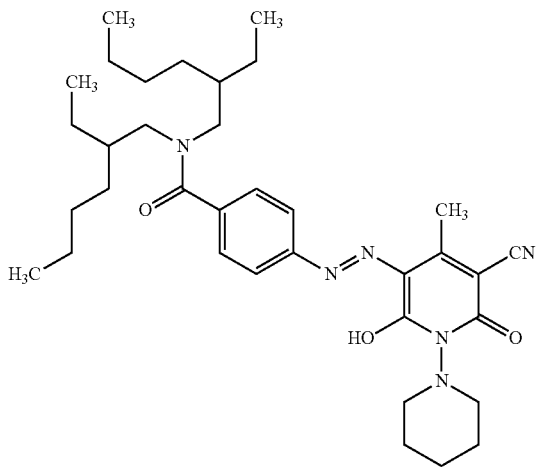

-continued
Compound (12)
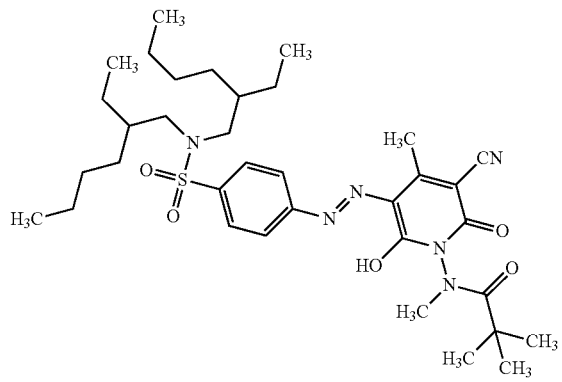
Compound (13)
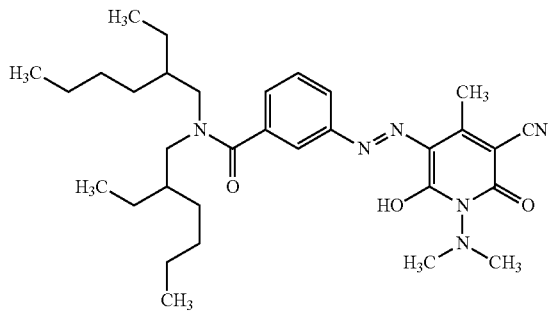
Compound (14)
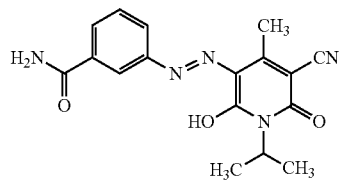
Compound (15)
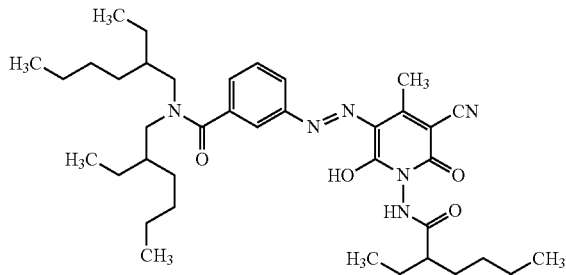
Compound (16)
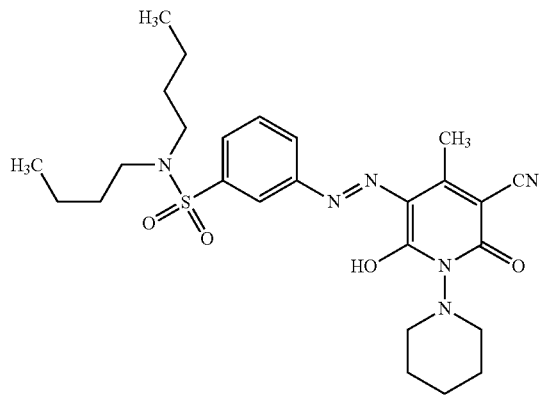
Compound (17)
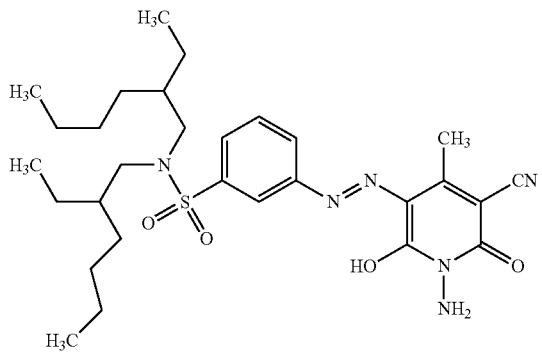
Compound (18)
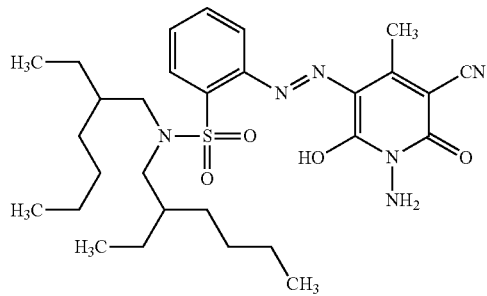

[Chem. 8]
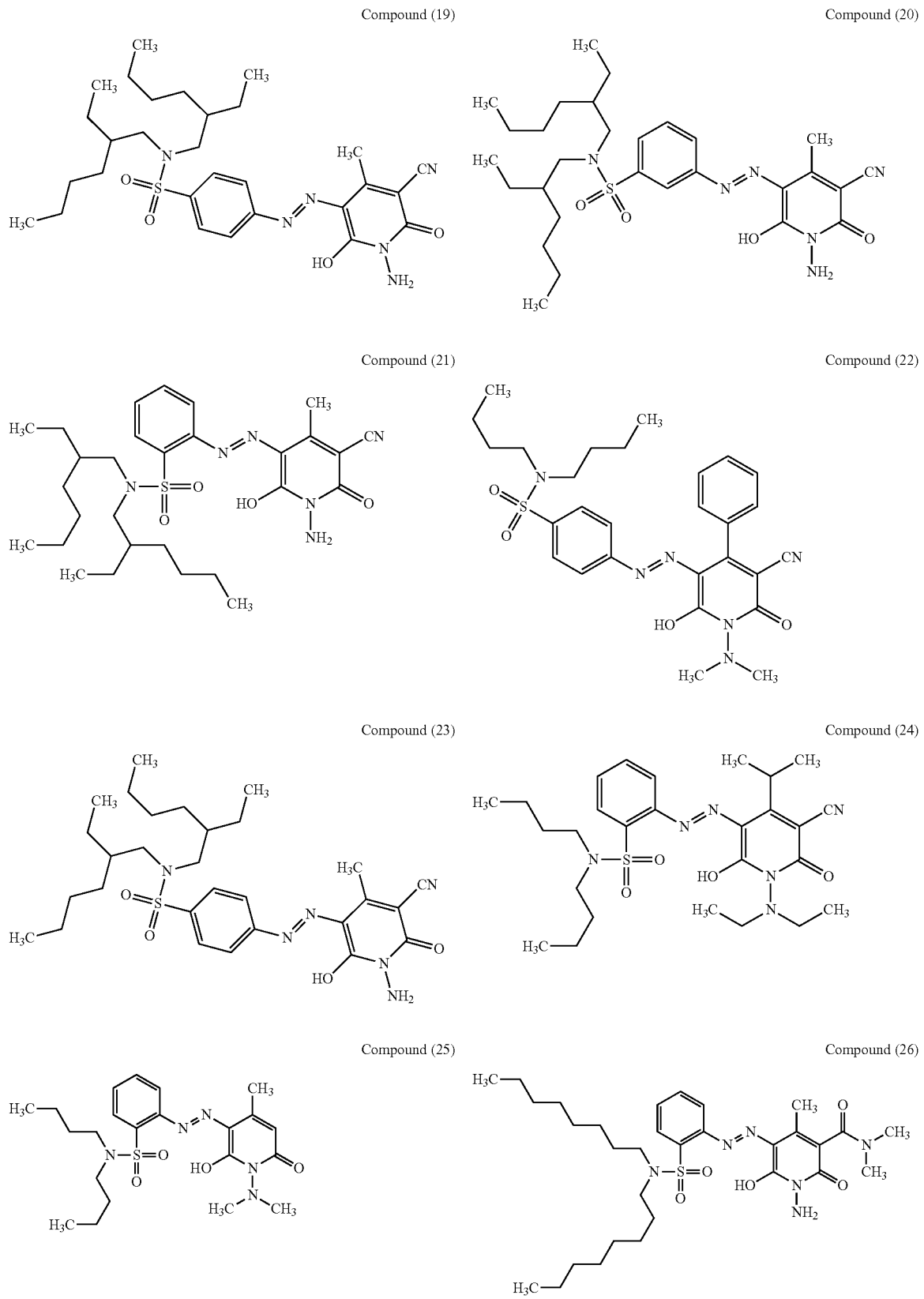

Compound (27)
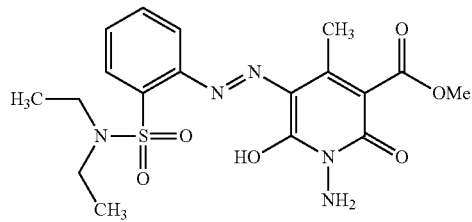
Compound (28)
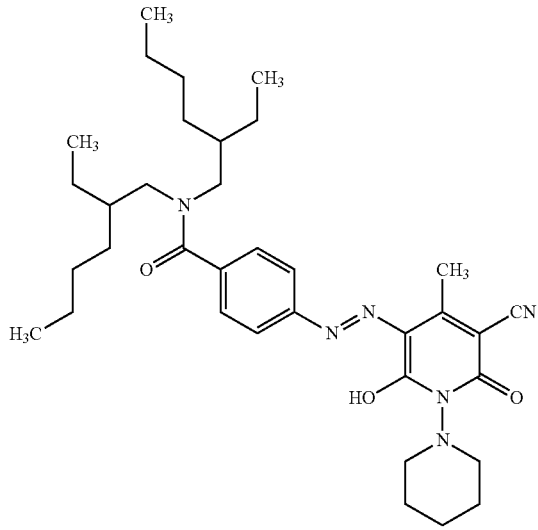
Compound (29)
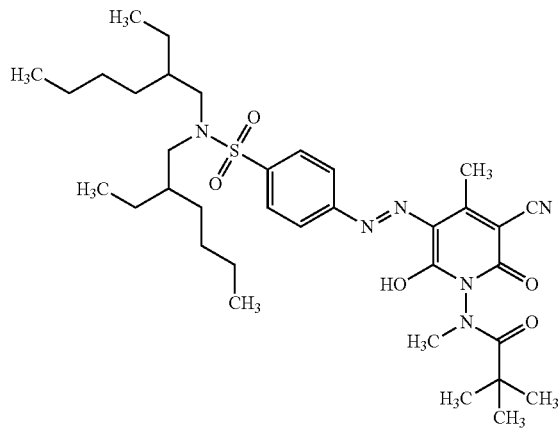
Compound (30)
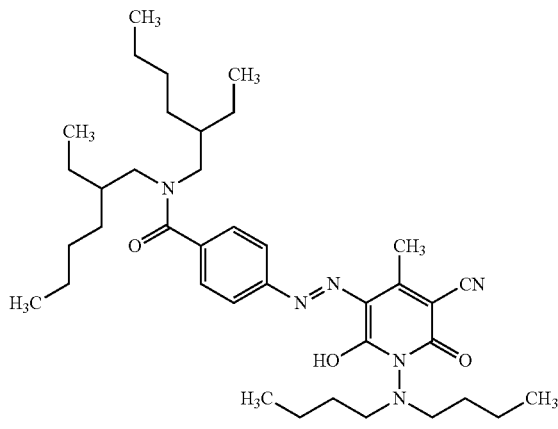
Compound (31)
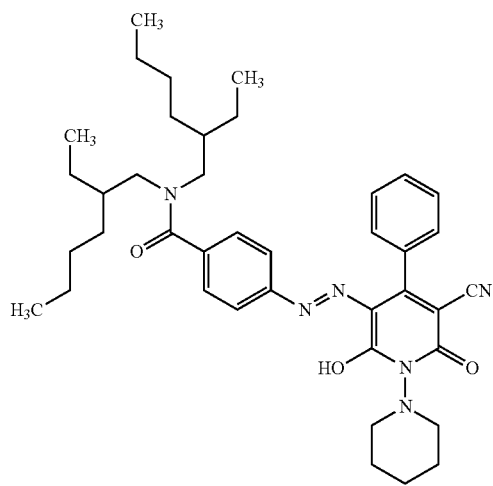
Compound (32)
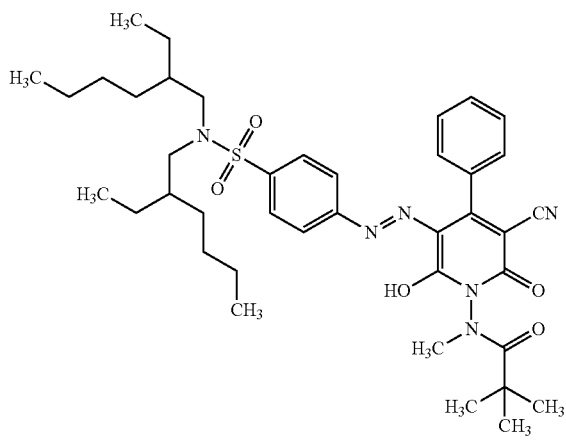

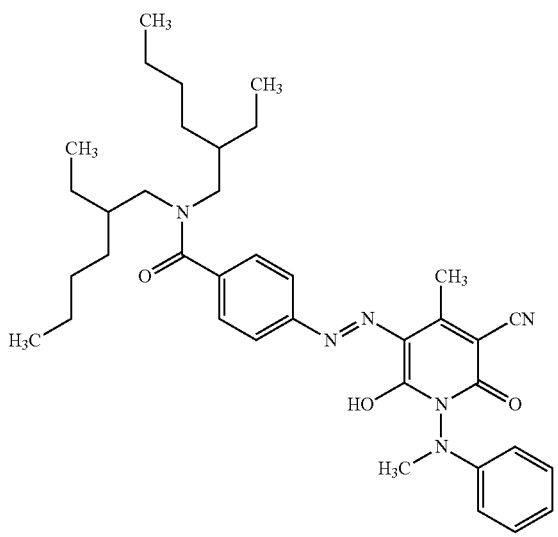

Compound (33)

Ink

The ink of the present invention will be described.

The water-insoluble coloring compound having a structure represented by Formula (1) of the present invention has excellent light resistance and can be advantageously used as a coloring agent of an ink.

The ink of the present invention contains a medium and the water-insoluble coloring compound having a structure represented by Formula (1).

In the ink of the present invention, the structural components other than components described above can be determined depending on the use of the ink of the present invention. The ink may contain appropriate additives within the ranges that do not impair the characteristics of the ink in each use.

The ink of the present invention can be suitably used not only as an ink for ink jet printing but also as an ink for printing, painting, or writing. In particular, the ink can be suitably used as an ink for a color filter yellow resist composition or as an ink for a thermal transfer recording sheet, described below.

The ink of the present invention can be prepared as follows.

A water-insoluble coloring compound of the present invention and optional another coloring agent, an emulsifier, and a resin are gradually added to a medium with stirring for mixing these components with the medium thoroughly and evenly. Furthermore, a mechanical shear force is applied to the mixture with a dispersing machine to allow the components to be dissolved or finely dispersed in a stable state to give an ink of the present invention.

In the present invention, the term "medium" refers to water or an organic solvent.

In the case of using an organic solvent as the medium of the ink of the present invention, the type of the organic solvent is determined depending on the intended use of the coloring agent and is not particularly limited. Examples of the organic solvent include alcohols such as methanol, ethanol, denatured ethanol, isopropanol, n-butanol, isobutanol, tert-butanol, sec-butanol, 2-methyl-2-butanol, 3-pentanol, octanol, benzyl alcohol, and cyclohexanol; glycols such as methyl cellosolve, ethyl cellosolve, diethylene glycol, and diethylene glycol monobutyl ether; ketones such as acetone, methyl ethyl ketone, and methyl isobutyl ketone; esters such as ethyl acetate, butyl acetate, ethyl propionate, and cellosolve acetate; aliphatic hydrocarbons such as hexane, octane, petroleum ether, and cyclohexane; aromatic hydrocarbons such as benzene, toluene, and xylene; halogenated hydrocarbons such as carbon tetrachloride, trichloroethylene, and tetrabromoethane; ethers such as diethyl ether, dimethyl glycol, trioxane, and tetrahydrofuran; acetals such as methylal and diethyl acetal; organic acids such as formic acid, acetic acid, and propionic acid; and sulfur- or nitrogen-containing organic compounds such as nitrobenzene, dimethylamine, monoethanolamine, pyridine, dimethyl sulfoxide, and dimethylformamide.

The organic solvent that can be used in the ink of the present invention may be a polymerizable monomer. The polymerizable monomer is an addition polymerizable or condensation polymerizable monomer and, in particular, can be an addition polymerizable monomer. Examples of the polymerizable monomer include styrene monomers such as styrene, α-methyl styrene, α-ethylstyrene, o-methylstyrene, m-methylstyrene, p-methylstyrene, o-ethylstyrene, m-ethylstyrene, and p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, and amide acrylate; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, and amide methacrylate; olefin monomers such as ethylene, propylene, butylene, butadiene, isoprene, isobutylene, and cyclohexene; halogenated vinyl monomers such as vinyl chloride, vinylidene chloride, vinyl bromide, and vinyl iodide; vinyl ester monomers such as vinyl acetate, vinyl propionate, and vinyl benzoate; vinyl ether monomers such as vinyl methyl ether, vinyl ethyl ether, and vinyl isobutyl ether; and vinyl ketone monomers such as vinyl methyl ketone, vinyl hexyl ketone, and methyl isopropenyl ketone. These monomers may be used alone or optionally in combination of two or more thereof.

As the coloring agent constituting the ink of the present invention, the water-insoluble coloring compound having a structure represented by Formula (1) is used. The ink can optionally contain another coloring agent that does not impair the solubility or dispersibility of the water-insoluble coloring compound in a medium.

Examples of the optional coloring agent that can be contained in the ink include, but are not limited to, C.I. Solvent Yellow 1, 19, 44, 49, 62, 74, 77, 79, 81, 82, 83, 89, 90, 93, 98, 103, 104, 112, 120, 121, 151, 153, 154, and 162; C.I. Pigment Yellow 1, 2, 3, 4, 5, 6, 7, 10, 11, 12, 13, 14, 15, 17, 23, 62, 65, 73, 74, 81, 83, 93, 94, 95, 97, 98, 109, 110, 111, 117, 120, 127, 128, 129, 137, 138, 139, 147, 150, 151, 154, 155, 167, 168, 173, 174, 176, 180, 181, 183, and 191; and various coloring agents classified as derivatives thereof.

The content of the coloring agent contained in the ink of the present invention can be 1.0 to 30.0 parts by mass, such as 2.0 to 20.0 parts by mass, and even 3.0 to 15.0 parts by mass, based on 100.0 parts by mass of the medium. In such a range, sufficient tinting strength is provided, and also satisfactory dispersibility of the coloring agent is achieved.

In the case of using water as the medium of the ink of the present invention, the ink can optionally contain an emulsifier for achieving satisfactory dispersion stability of the coloring agent. Examples of the usable emulsifier include, but are not limited to, cationic surfactants, anionic surfactants, and nonionic surfactants.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soaps such as sodium stearate and sodium dodecanoate; sodium dodecyl sulfate; sodium dodecyl benzene sulfate; and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

The ink of the present invention can further contain a resin. The type of the resin that can be contained in the ink of the present invention is determined depending on the intended use and is not particularly limited. Examples of the resin include polystyrene resins, styrene copolymers, polyacrylic acid resins, polymethacrylic acid resins, polyacrylic resins, polymethacrylic resins, acrylic acid copolymers, methacrylic acid copolymers, polyester resins, polyvinyl ether resins, polyvinyl methyl ether resins, polyvinyl alcohol resins, polyvinyl butyral resins, polyurethane resins, and polypeptide resins. These resins may be used alone or optionally in combination of two or more thereof.

Any dispersing machine can be used in production of the ink without limitation. For example, a rotation shearing-type homogenizer, a media type dispersing machine such as a ball mill, a sand mill, or an attritor, or a high-pressure counter-collision type dispersing machine can be used.

As described above, the ink of the present invention contains the water-insoluble coloring compound of the present invention and thereby has excellent light resistance.

Thermal Transfer Recording Sheet

The thermal transfer recording sheet of the present invention will now be described.

The water-insoluble coloring compound of the present invention has excellent light resistance and therefore can be suitably applied to a thermal transfer recording sheet.

The thermal transfer recording sheet of the present invention includes a base material and a coloring material layer formed on the base material from a composition containing the water-insoluble coloring compound of the present invention.

The thermal transfer recording sheet of the present invention can be prepared as follows. A coloring agent containing the water-insoluble coloring compound having a structure represented by Formula (1) and a binder resin and optionally a surfactant and a wax are gradually added to a medium with stirring for mixing these components with the medium thoroughly and evenly. Furthermore, a mechanical shear force is applied to the mixture with a dispersing machine to allow the components to be dissolved or finely dispersed in a stable state to prepare the ink of the present invention. Subsequently, the ink is applied to a base film as the base material and dried to produce a thermal transfer recording sheet of the present invention, but the present invention is not limited to the thermal transfer recording sheet produced by this method as long as the thermal transfer recording sheet includes the water-insoluble coloring compound having a structure represented by Formula (1).

Various resins can be used as the binder resin for the coloring material layer of the thermal transfer recording sheet of the present invention. Specific examples thereof include water-soluble resins such as cellulose resins, polyacrylic acid resins, starch resins, and epoxy resins; and organic solvent-soluble resins such as polyacrylic resins, polymethacrylic resins, polystyrene resins, polycarbonate resins, polyether sulfone resins, polyvinyl butyral resins, ethyl cellulose resins, acetyl cellulose resins, polyester resins, AS resins, and phenoxy resins. These resins may be used alone or optionally in combination of two or more thereof.

The solvent used in the method of producing the thermal transfer recording sheet may be the same as those that are used as the solvent of the ink. Specific examples of the medium include water and organic solvents. Examples of the organic solvent include alcohols such as methanol, ethanol, isopropanol, and isobutanol; cellosolves such as methyl cellosolve and ethyl cellosolve; aromatic hydrocarbons such as toluene, xylene, and chlorobenzene; esters such as ethyl acetate and butyl acetate; ketones such as acetone, methyl ethyl ketone, methyl isobutyl ketone, and cyclohexanone; halogenated hydrocarbons such as methylene chloride, chloroform, and trichloroethylene; ethers such as tetrahydrofuran and dioxane; N,N-dimethylformamide; and N-methylpyrrolidone. The organic solvents may be used alone or optionally in combination of two or more thereof.

The thermal transfer recording sheet of the present invention contains the water-insoluble coloring compound having a structure represented by Formula (1) as the coloring agent and thereby has excellent light resistance. Furthermore, the thermal transfer recording sheet may contain another coloring agent for toning in order to provide desired spectral characteristics. Any optional coloring agent that does not highly affect the brightness, saturation, and light resistance of the thermal transfer recording sheet of the present invention can be used without limitation, and examples thereof include C.I. Solvent Yellow 1, 19, 44, 49, 62, 74, 77, 79, 81, 82, 83, 89, 90, 93, 98, 103, 104, 112, 120, 121, 151, 153, 154, and 162; and various coloring agents classified as derivatives thereof.

The mass ratio of the binder resin to the coloring agent (the use ratio of (binder resin):(coloring agent)) can be in a range of 1:2 to 2:1, from the viewpoint of a transferring property.

The thermal transfer recording sheet of the present invention may contain a surfactant for having a sufficient lubricating property during heating the thermal head (during printing). Examples of the surfactant that can be contained in the thermal transfer recording sheet include cationic surfactants, anionic surfactants, and nonionic surfactants.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soaps such as sodium stearate and sodium dodecanoate; sodium dodecyl sulfate; sodium dodecyl benzene sulfate; and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

The thermal transfer recording sheet of the present invention may contain a wax for having a sufficient lubricating property during non-heating the thermal head. Examples of the wax that can be contained in the thermal transfer recording sheet include, but are not limited to, polyethylene waxes, paraffin waxes, and fatty acid ester waxes.

The thermal transfer recording sheet of the present invention may optionally contain an ultraviolet absorber, an antiseptic, an antioxidant, an anti-static agent, or a viscosity modifier, in addition to the above-described additives.

Any base film can be used as the base material for the thermal transfer recording sheet of the present invention without limitation. For example, thin paper such as condenser paper or glassine paper or a plastic film of polyester, polycarbonate, polyamide, polyimide, or polyaramide can be used from the viewpoint of high heat resistance; and a polyethylene terephthalate film can be used from the viewpoints of mechanical strength, solvent resistance, and cost performance. The thickness of the base material can be 3 to 50 μm from the viewpoint of a transferring property.

The thermal transfer recording sheet of the present invention can have a layer of a lubricant, a heat-resistant fine particles having a high lubricating property, and a thermal resin such as a binding agent on the opposite side of the base material from the coloring material layer, for increasing the heat resistance and the mobility of the thermal head. Examples of the lubricant include, but are not limited to, amino-modified silicone compounds and carboxy-modified silicone compounds. Examples of the heat-resistant fine particles include, but are not limited to, fine particles such as silica, and examples of the binding agent include, but are not limited to, acrylic resins.

Any dispersing machine can be used in the dispersing step without limitation. For example, a rotation shearing-type homogenizer, a media type dispersing machine such as a ball mill, a sand mill, and an attritor, or a high-pressure countercollision type dispersing machine can be used.

The ink composition may be applied to the base film by any method without limitation, for example, a method using a bar coater, a gravure coater, a reverse roll coater, a rod coater, or an air doctor coater. The application amount of the ink composition can be controlled so that the coloring material layer after drying has a thickness of 0.1 to 5 μm, from the viewpoint of a transferring property.

The thermal transfer recording sheet of the present invention may be heated by any method without limitation. For example, not only a thermal head, which is usually used, but also infrared rays or a laser can be used. Alternatively, an electrical conduction exothermic film that generates heat by electrifying the base film itself may be used as an electrical conduction-type dye transfer sheet.

As described above, the thermal transfer recording sheet of the present invention having excellent light resistance can be provided.

Color Filter Resist Composition

The color filter resist composition of the present invention will now be described.

The water-insoluble coloring compound of the present invention has excellent light resistance and therefore can be suitably applied to a color filter resist composition.

The color filter resist composition of the present invention contains a binder resin, a solvent, and the water-insoluble coloring compound of the present invention.

The color filter resist composition of the present invention is prepared as follows. The water-insoluble coloring compound and a binder resin are added to a solvent with stirring. The color filter resist composition may optionally contain a polymerizable monomer, a polymerization initiator, and a photoacid generator. Subsequently, a mechanical shear force is applied to the mixture with a dispersing machine to allow the components to be dissolved or finely dispersed in a stable state to give the color filter resist composition of the present invention.

Any binder resin can be used in the color filter resist composition of the present invention, as long as either a light-irradiating portion or a light-shielding portion in the exposure process of pixel formation is soluble in an organic solvent, an alkali aqueous solution, water, or a commercially available developing solution. In particular, a resin having a composition that allows developing in water or an alkali aqueous solution can be used from the viewpoint of workability and treatment after resist production.

The usable binder resin can be formed by copolymerizing a hydrophilic polymerizable monomer and a hydrophobic polymerizable monomer at an appropriate mixing ratio by a known method. Typical examples of the hydrophilic polymerizable monomer include acrylic acid, methacrylic acid, N-(2-hydroxyethyl)acrylamide, N-vinylpyrrolidone, and polymerizable monomers having ammonium salts. Typical examples of the hydrophobic polymerizable monomer include acrylic acid ester, methacrylic acid ester, vinyl acetate, styrene, and N-vinylcarbazole. Such a binder resin can be used as a negative-type resist where the solubility of materials of the exposure portion in a developing solution is decreased by exposure to light and thereby only the light-shielding portion is removed by developing, by combining a radical polymerizable monomer having an ethyleny unsaturated group, a cationic polymerizable monomer having an oxirane ring or an oxetane ring, a radical-generating agent, an acid-generating agent, and a base-generating agent.

In addition, a combination of
an acid-generating agent that generates an acid by exposure to light, and
at least one of
a resin having a quinone diazide group that is cleaved by light and generates a carboxylic acid group;
tert-butylcarbonate of polyhydroxystyrene; and
a binder resin having a group that is cleaved by an acid such as tetrahydropyranyl ether, can be used.

The solubility of the above mentioned resins to a developing solution will increase when they are exposed with light. Thus, the resins are suitable for a positive resist of which only a light exposed portion is removed by development.

When the color filter resist composition of the present invention is a negative-type resist composition, a polymerizable monomer that is addition-polymerized by exposure to light (hereinafter, also referred to as a photopolymerizable monomer) can be used. The photopolymerizable monomer can be a compound having at least one addition polymerizable ethyleny unsaturated double bond in the molecule and having a boiling point of 100° C. or more at ordinary pressure. Examples of the photopolymerizable monomer include monofunctional acrylates and methacrylates such as polyethylene glycol monoacrylate, polyethylene glycol monomethacrylate, polypropylene glycol monoacrylate, polypropylene glycol monomethacrylate, phenoxyethyl acrylate, and phenoxyethyl methacrylate; multi-functional acrylates and methacrylates such as polyethylene glycol diacrylate, polyethylene glycol dimethacrylate, polypropylene glycol diacrylate, polypropylene glycol dimethacrylate, trimethylol ethane triacrylate, trimethylol ethane trimethacrylate, trimethylol propane triacrylate, trimethylol propane trimethacrylate, trimethylol propane diacrylate, trimethylol propane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylol propane tri(acryloyloxypropyl)ether, tri(acryloyloxyethyl) isocyanurate, tri(acryloyloxyethyl)cyanurate, glycerin triacrylate, and glycerin trimethacrylate; and multi-functional acrylates and methacrylates obtained by adding ethylene oxide or propylene oxide to a multi-functional alcohol such as trimethylol propane or glycerin and then performing acrylation or methacrylation. Examples of the photopolymerizable monomer further include multi-functional epoxy acrylates and epoxy methacrylates, which are reaction products of acrylic acid or methacrylic acid with a urethane acrylate, a polyester acrylate, or an epoxy resin. In particular, trimethylol propane triacrylate, trimethylol propane trimethacrylate, pentaerythritol tetraacrylate, pentaerythritol tetramethacrylate, dipentaerythritol hexaacrylate, dipentaerythritol hexamethacrylate, dipentaerythritol pentaacrylate, and dipentaerythritol pentamethacrylate can be used.

The above-mentioned photopolymerizable monomers may be used alone or optionally in combination of two or more thereof.

The content of the photopolymerizable monomer may be 5 to 50% by mass, such as 10 to 40% by mass, based on the mass of the resist composition (the entire solid content excluding the solvent) of the present invention. A content of 5 to 50% by mass can further enhance the sensitivity to exposure and the strength of pixels and can allow the adhesiveness of the resist composition to be in an appropriate state.

When the color filter resist composition of the present invention is a negative-type resist composition, the composition may contain a photopolymerization initiator. Examples of the photopolymerization initiator include a vicinal polyketoaldonyl compounds, α-carbonyl compounds, asioin ethers, various quinone compounds, combinations of triallylimidazole dimers and p-aminophenylketone, and trioxadiazole compounds. In particular, 2-benzyl-2-dimethylamino-1-(4-morpholinophenyl)butanone (Trade name: Irgacure 369, manufactured by BASF AG) can be used. When electron rays are used for pixel formation with a color resist of the present invention, the photopolymerization initiator is not essential.

When the color filter resist composition of the present invention is a positive-type resist composition, the composition may optionally contain a photoacid generator. The photoacid generator may be a known one, and examples of the usable photoacid generator include salts of anions and onium ions such as sulfonium, iodonium, selenium, ammonium, and phosphonium.

Examples of the sulfonium ion include triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyltetrahydrothiophenium.

Examples of the iodonium ion include diphenyliodonium, di-p-tolyliodonium, bis(4-dodecylphenyl)iodonium, bis(4-methoxyphenyl)iodonium, and (4-octyloxyphenyl)phenyliodonium.

Examples of the selenium ion include triarylseleniums (e.g., triphenylselenium, tri-p-tolylselenium, tri-o-tolylselenium, tris(4-methoxyphenyl)selenium, 1-naphthyldiphenylselenium, tris(4-fluorophenyl) selenium, tri-1-naphthylselenium, and tri-2-naphthylselenium).

Examples of the ammonium ion include tetraalkylammoniums (e.g., tetramethylammonium, ethyltrimethylammonium, diethyldimethylammonium, triethylmethylammonium, tetraethylammonium, trimethyl-n-propylammonium, trimethylisopropylammonium, trimethyl-n-butylammonium, and trimethylisobutylammonium).

Examples of the phosphonium ion include tetraphenylphosphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, and tetraethylphosphonium.

Examples of the anion include, but are not limited to, perhalogenic acid ions such as $ClO_4^-$ and $BrO_4^-$; halogenated sulfonate ions such as $FSO_3^-$ and $ClSO_3^-$; sulfate ions such as $CH_3SO_4^-$, $CF_3SO_4^-$, and $HSO_4^-$; carbonate ions such as $HCO_3^-$ and $CH_3CO_3^-$; aluminate ions such as $AlCl_4^-$ and $AlF_4^-$; a hexafluorobismuthic acid ion; carboxylate ions such as $CH_3COO^-$, $CF_3COO^-$, $C_6H_3COO^-$, $CH_3C_6H_4COO^-$, $C_6F_3COO^-$, and $CF_3C_6H_4COO^-$; arylborate ions such as $B(C_6H_5)_4^-$ and $CH_3CH_2CH_2CH_2B(C_6H_5)_3^-$; a thiocyanate ion; and a nitrate ion.

In the color filter resist composition of the present invention, examples of the medium for dissolving or dispersing the water-insoluble coloring compound, the binder resin, and optional photopolymerizable monomer, photopolymerization initiator, and photoacid generator include water and various organic solvents. Examples of the organic solvent include cyclohexanone, ethyl cellosolve acetate, butyl cellosolve acetate, 1-methoxy-2-propyl acetate, diethylene glycol dimethyl ether, ethyl benzene, 1,2,4-trichlorobenzene, ethylene glycol diethyl ether, xylene, ethyl cellosolve, methyl-n-amyl ketone, propylene glycol monomethyl ether, toluene, methyl ethyl ketone, ethyl acetate, methanol, ethanol, isopropanol, butanol, methyl isobutyl ketone, and petroleum solvents. These organic solvents can be used alone or in combination of two or more thereof. The medium of the color filter resist composition of the present invention may be the same as or different from the medium used together with the water-insoluble coloring compound as long as the dispersibility of the coloring agent is not impaired.

In a color filter where two or more types of pixels having different spectral characteristics are arranged so as to be adjacent to each other, the color filter can have excellent light resistance by using the resist composition of the present invention in the pixels constituting at least one color among the plurality of colors (e.g., red, green, and blue) of the pixels. In order to provide desired spectral characteristics, the composition may contain another dye for tone adjustment. Any dye can be used as the additional dye without limitation, and examples of the dye include C.I. Solvent Blue 14, 24, 25, 26, 34, 37, 38, 39, 42, 43, 44, 45, 48, 52, 53, 55, 59, 67, and 70;

and C.I. Solvent Red 8, 27, 35, 36, 37, 38, 39, 40, 49, 58, 60, 65, 69, 81, 83:1, 86, 89, 91, 92, 97, 99, 100, 109, 118, 119, 122, 127, and 218.

The color filter resist composition of the present invention may contain an ultraviolet absorber and a silane coupling agent for improving adhesiveness with a glass substrate in the process of producing the filter, as necessary, in addition to the above-described additives.

Any dispersing machine may be used for producing the resist solution containing the resist composition without limitation. For example, a rotation shearing-type homogenizer, a media type dispersing machine such as a ball mill, a sand mill, or an attritor, or a high-pressure counter-collision type dispersing machine can be used.

As described above, the color filter resist composition of the present invention contains the water-insoluble coloring compound having a bright yellow color tone of the present invention. Hence, a color filter resist composition having excellent light resistance can be provided.

EXAMPLES

The present invention will be described in more detail by the following Examples and Comparative Examples, but is not limited to these Examples. Note that "part(s)" and "%" in Examples and Comparative Examples are based on mass unless otherwise specified. The prepared reaction products were identified using a $^1$H nuclear magnetic resonance CH NMR) spectrometer (ECA-400, manufactured by JEOL Ltd.) and matrix-assisted laser desorption-ionization mass spectrometer (MALDI-TOF-MS) (autoflex apparatus, manufactured by Bruker Daltonics K.K.). In the MALDI-TOF-MS, the negative mode was employed for detecting ions. Production of water-insoluble coloring compound having a structure represented by Formula (1)

The water-insoluble coloring compound having a structure represented by Formula (1) of the present invention can be synthesized by a known process.

The water-insoluble coloring compounds each having a structure represented by Formula (1) of the present invention were produced by the process described below. Furthermore, the solubilities of each of the resulting water-insoluble coloring compounds in water at room temperature and at 60° C. were measured and were confirmed to be less than 1% by mass.

Example 1

Production of Compound (1)

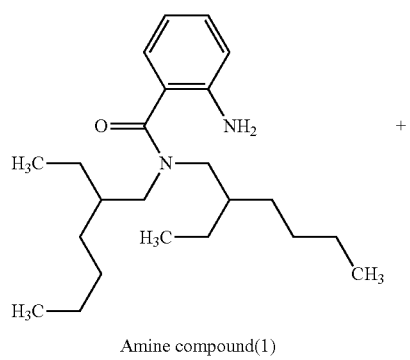

Amine compound(1)

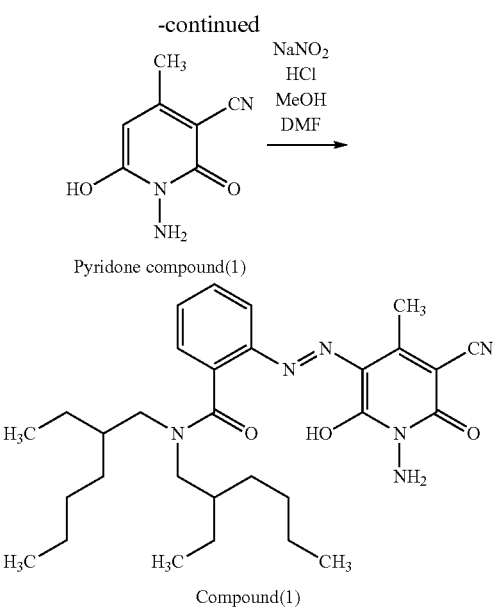

Pyridone compound(1)

Compound(1)

A solution of 3.61 g of amine compound (1) in 20 mL of methanol (MeOH) was cooled to 5° C., and 2.65 mL of 35% hydrochloric acid was dropwise added thereto. Furthermore, a solution of 0.76 g of sodium nitrite in 3 mL of water was dropwise added thereto (diazotized solution A). Separately, a solution of 1.65 g of pyridone compound (1) in 8 mL of N,N-dimethylformamide (DMF) was cooled to 5° C., and diazotized solution A was slowly dropwise added thereto while maintaining the temperature at 5° C. or less, followed by stirring at 0 to 5° C. for further 3 hours. After the completion of the reaction, a sodium carbonate aqueous solution was dropwise added to the reaction solution to neutralize the solution to pH 6. The precipitated solid was collected by filtration and was further washed with water. The resulting solid was purified by column chromatography (eluent: heptane/ethyl acetate) and was recrystallized from a heptane solution to yield 1.4 g of Compound (1). Analytical results of Compound (1)

[1] $^1$H-NMR (400 MHz, CDCl$_3$, at room temperature): δ (ppm)=15.12 (1H, s), 7.88 (1H, d, J=8.39 Hz), 7.54-7.50 (1H, m), 7.33-7.29 (2H, m), 5.31 (2H, s), 3.72-3.32 (2H, br), 3.26 (2H, d, J=6.48 Hz), 2.64 (3H, s), 1.83 (1H, s), 1.51-1.30 (9H, m), 1.12-0.75 (14H, m), 0.74 (3H, s), 0.62 (3H, s).

[2] Mass spectrometry by MALDI-TOF-MS: m/z=535.617 (M−H)$^-$

Example 2

Production of Compound (4)

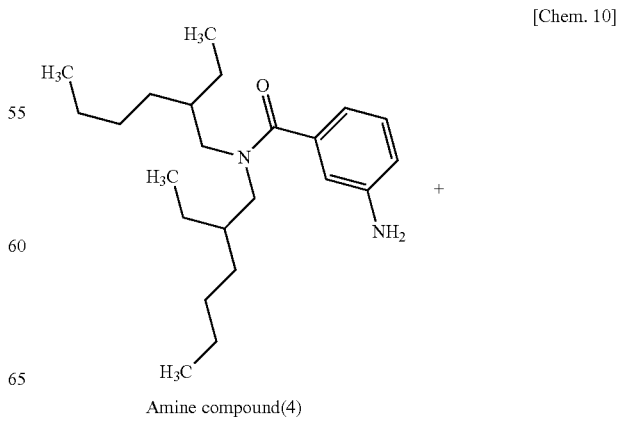

Amine compound(4)

-continued

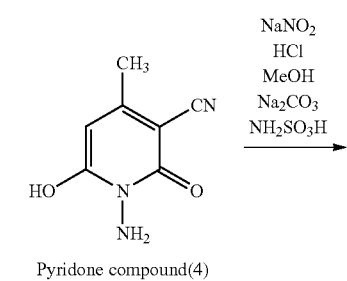

Pyridone compound(4)

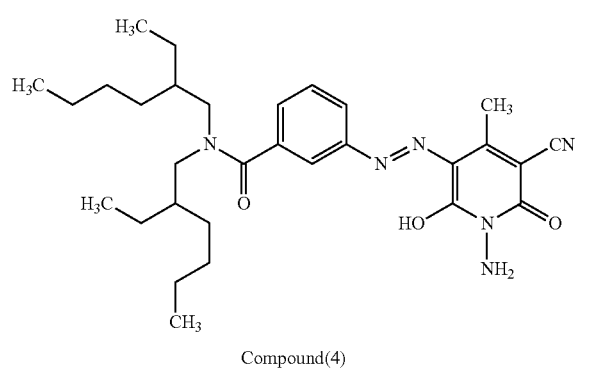

Compound(4)

A solution of 3.61 g of amine compound (4) in 20 mL of methanol (MeOH) was cooled to 5° C., and 2.65 mL of 35% hydrochloric acid was dropwise added thereto. Furthermore, a solution of 0.76 g of sodium nitrite in 3 mL of water was dropwise added thereto, followed by stirring for 1 hour. Furthermore, 0.117 g of amidosulfuric acid was added thereto to decompose excess sodium nitrite to prepare diazotized solution B. Separately, a solution of 1.65 g of pyridone compound (4) in 8 mL of dimethylformamide was cooled to 5° C., and diazotized solution B was slowly dropwise added thereto while maintaining the temperature at 5° C. or less, followed by stirring at 0 to 5° C. for further 3 hours. After the completion of the reaction, a sodium carbonate aqueous solution was dropwise added to the reaction solution to neutralize the solution to pH 6, followed by extraction with chloroform. The chloroform layer was concentrated. The resulting solid was purified by column chromatography (eluent: heptane/chloroform) and was recrystallized from a heptane/chloroform solution to yield 2.5 g of Compound (4).

Analytical Results of Compound (4)

[1] $^1$H-NMR (400 MHz, CDCl$_3$, room temperature): δ (ppm)=14.99 (1H, s), 7.52-7.48 (3H, m), 7.29 (1H, s), 5.27 (2H, s), 3.46 (2H, d, J=5.72 Hz), 3.17 (2H, d, J=6.87 Hz), 2.63 (3H, s), 1.84-1.75 (1H, br), 1.59-1.49 (1H, br), 1.47-1.28 (9H, s), 1.24-1.16 (3H, br), 1.13-1.02 (4H, br), 0.98-0.92 (6H, m), 0.83 (3H, t, J=7.25 Hz), 0.72 (3H, t, J=7.44 Hz).

[2] Mass spectrometry by MALDI-TOF-MS: m/z=535.457 (M−H)$^-$

Example 3

Production of Compound (8)

[Chem. 11]

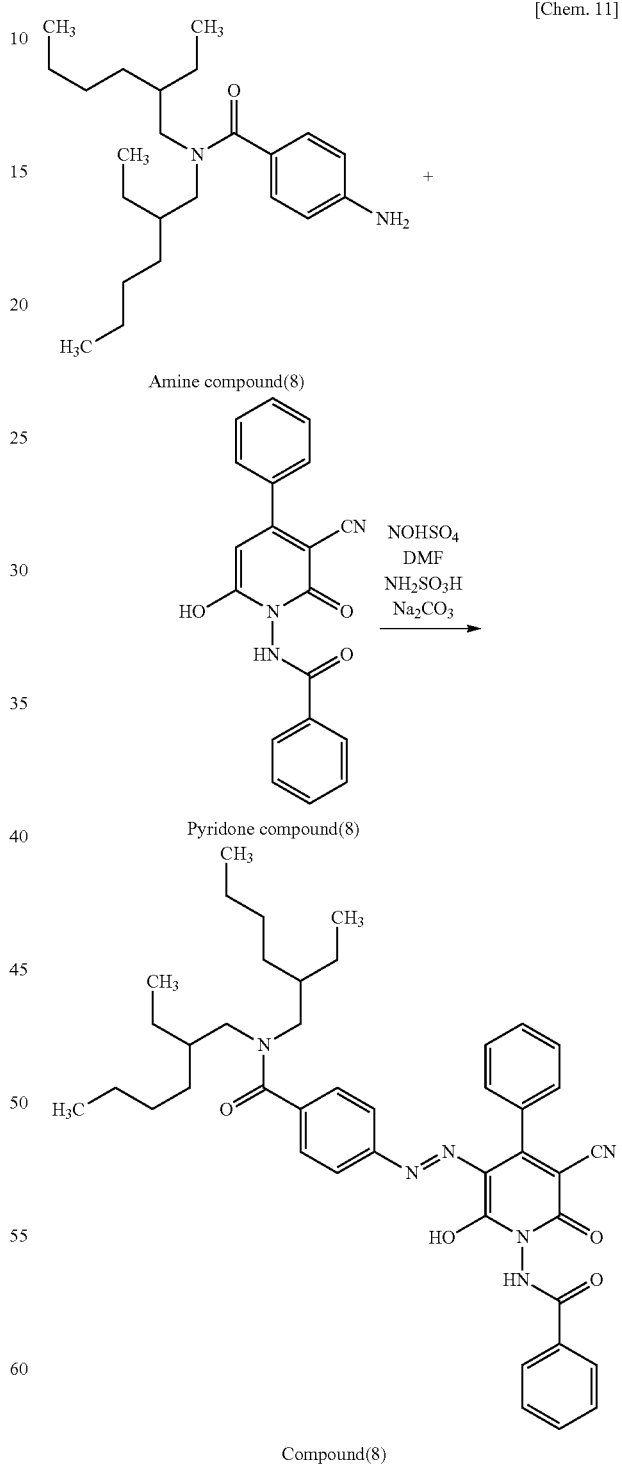

A solution of 3.61 g of amine compound (8) in 20 mL of N,N-dimethylformamide (DMF) was cooled to 5° C., and 20 mL of a 40% nitrosylsulfuric acid solution in N,N-dimethylformamide was slowly dropwise added thereto. Furthermore, a solution of 0.76 g of sodium nitrite in 3 mL of water was dropwise added thereto, followed by stirring for 1 hour. Furthermore, 0.117 g of amidosulfuric acid was added thereto to decompose excess nitrosylsulfuric acid to prepare diazotized solution C. Separately, a solution of 3.31 g of pyridone compound (8) in 8 mL of dimethylformamide was cooled to 5° C., and diazotized solution C was slowly dropwise added thereto while maintaining the temperature at 5° C. or less, followed by stirring at 0 to 5° C. for further 3 hours. After the completion of the reaction, extraction with chloroform was performed. The chloroform layer was concentrated, and the resulting solid was purified by column chromatography (eluent: heptane/chloroform) and was recrystallized from a heptane/chloroform solution to yield 3 g of Compound (8).

Analytical Results of Compound (8)

[1] $^1$H-NMR (400 MHz, CDCl$_3$, room temperature): δ (ppm)=14.58 (1H, s), 9.71 (1H, s), 8.01 (2H, d, J=7.63 Hz), 7.60-7.53 (4H, m), 7.49-7.42 (4H, m), 7.32 (2H, d, J=8.39 Hz), 7.09 (2H, d, J=8.39 Hz), 3.53-3.30 (2H, m), 3.11 (2H, d, J=6.48 Hz), 1.79 (1H, s), 1.61-0.79 (26H, m), 0.68 (3H, s).

[2] Mass spectrometry by MALDI-TOF-MS: m/z=701.476 (M−H)$^−$

Example 4

Production of Compound (13)

Compound (13) was produced as in Example 1 except that amine compound (13) and pyridone compound (13) were respectively used in place of amine compound (1) and pyridone compound (1) in Example 1.

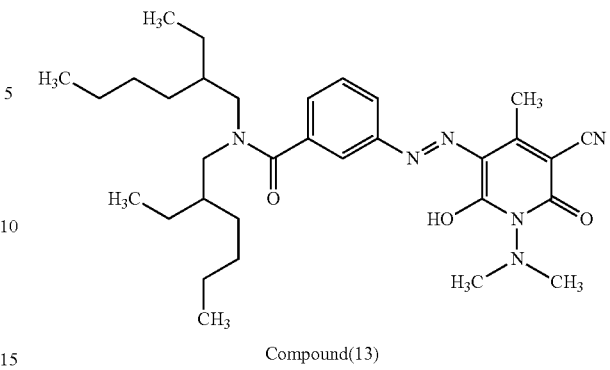

Compound(13)

Analytical Results of Compound (13)

[1] $^1$H-NMR (CDCl$_3$) δ (ppm): 14.99 (1H, s), 7.51-7.43 (3H, m), 7.25 (1H, s), 3.45 (2H, s), 3.17 (2H, d, J=6.87 Hz), 3.00 (6H, s), 2.59 (3H, s), 1.79-1.71 (1H, br), 1.61-1.50 (2H, br), 1.38-1.26 (8H, br), 1.24-1.18 (3H, br), 1.15-1.01 (4H, br), 0.98-0.88 (6H, m), 0.83 (3H, t, J=7.06 Hz), 0.71 (3H, t, J=7.25 Hz).

[2] Mass spectrometry: m/z=563.495 (M−H)$^−$

Example 5

Production of Compound (15)

Compound (15) was produced as in Example 1 except that amine compound (15) and pyridone compound (15) were respectively used in place of amine compound (1) and pyridone compound (1) in Example 1.

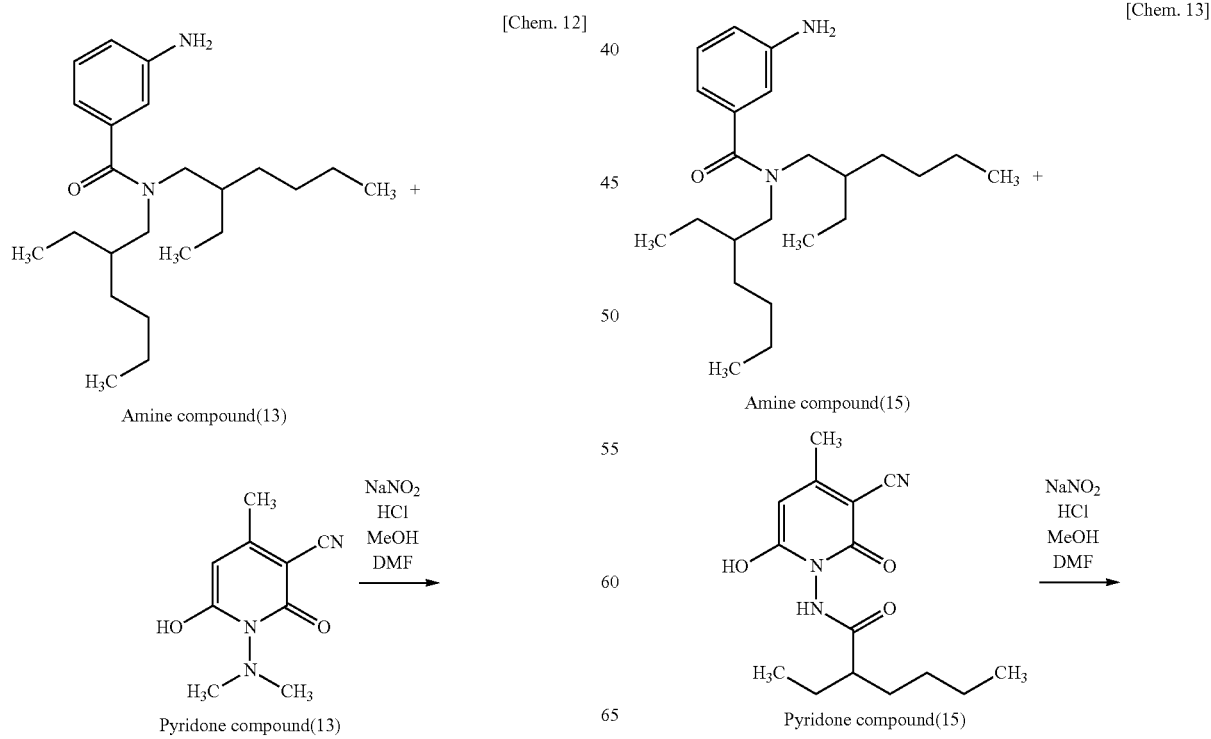

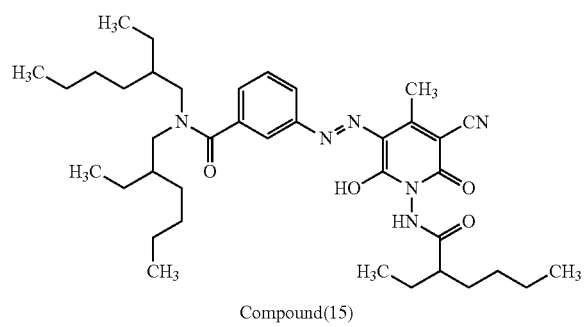

Compound(15)

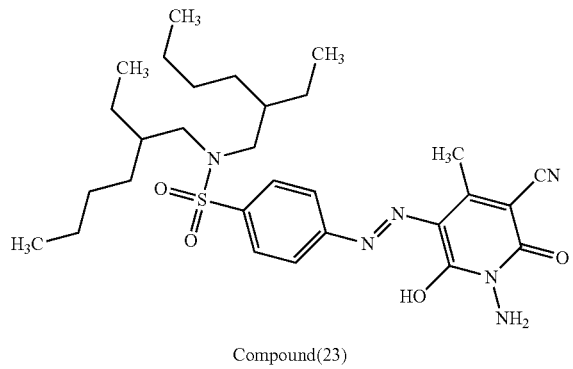

Compound(23)

Analytical Results of Compound (15)

[1] $^1$H-NMR (400 MHz, CDCl$_3$, room temperature): δ (ppm)=14.48 (1H, s), 9.92-9.72 (1H, br), 7.48 (1H, dd, J=7.63 Hz, J=7.65 Hz), 7.35 (1H, d, J=8.39 Hz), 7.23 (1H, s), 7.17 (1H, d, J=7.25 Hz), 3.62-3.31 (2H, m), 3.10 (2H, s), 2.55 (3H, s), 2.48-2.41 (1H, br), 1.88-1.82 (1H, br), 1.75-1.65 (2H, br), 1.54-1.25 (17H, m), 1.23-1.11 (3H, m), 1.09-0.94 (15H, m), 0.81 (3H, t, J=7.06 Hz), 0.68 (3H, d, J=9.16 Hz).

[2] Mass spectrometry by MALDI-TOF-MS: m/z=661.535 (M–H)$^-$

Analytical Results of Compound (23)

[1] $^1$H-NMR (400 MHz, CDCl$_3$, room temperature): δ (ppm)=14.90 (1H, s), 7.88 (2H, d, J=8.39 Hz), 7.54 (2H, d, J=8.39 Hz), 5.25 (2H, s), 3.04-2.86 (4H, m), 2.68 (3H, s), 1.63-1.51 (2H, br), 1.38-1.25 (16H, m), 0.94-0.78 (12H, m).

[2] Mass spectrometry by MALDI-TOF-MS: m/z=571.417 (M–H)$^-$

Example 6

Production of Compound (23)

Compound (23) was produced as in Example 1 except that amine compound (23) and pyridone compound (23) were respectively used in place of amine compound (1) and pyridone compound (1) in Example 1.

Example 7

Production of Compound (28)

Compound (28) was produced as in Example 1 except that amine compound (28) and pyridone compound (28) were respectively used in place of amine compound (1) and pyridone compound (1) in Example 1.

[Chem. 14]

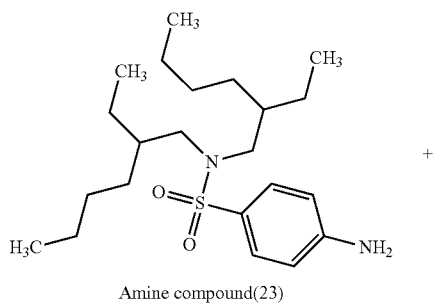

Amine compound(23)

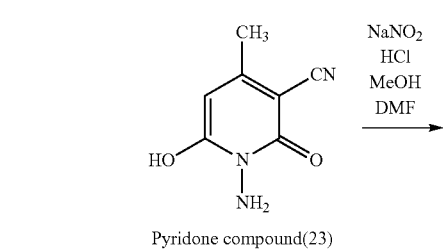

Pyridone compound(23)

[Chem. 15]

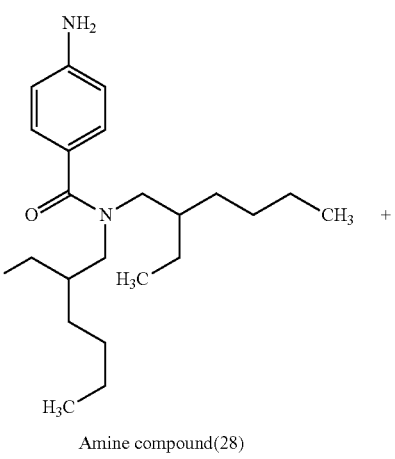

Amine compound(28)

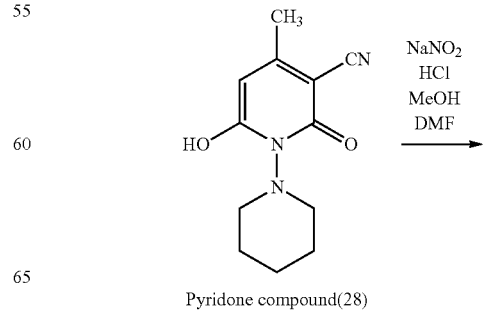

Pyridone compound(28)

-continued

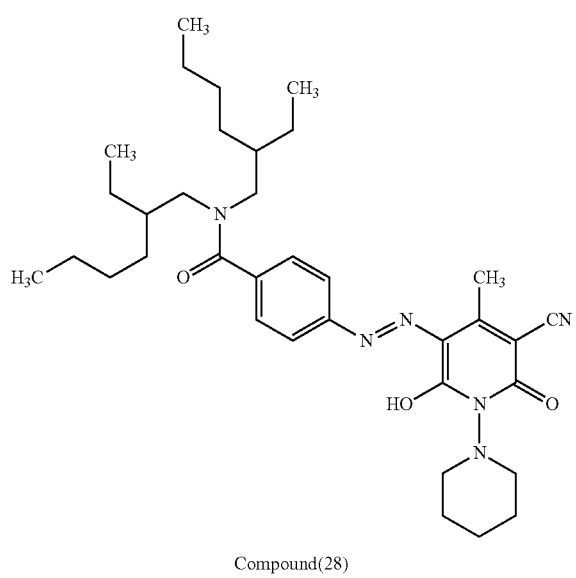

Compound(28)

Analytical Results of Compound (28)

[1] $^1$H-NMR (CDCl$_3$) δ (ppm): 14.98 (1H, s), 7.47 (4H, s), 3.56-3.49 (2H, m), 3.48-3.29 (2H, m), 3.28-3.20 (2H, m), 3.19-2.98 (2H, m), 2.60 (3H, s), 1.84-1.74 (4H, m), 1.73-1.65 (3H, m), 1.64-1.49 (1H, m), 1.48-1.25 (9H, m), 1.24-1.12 (3H, m), 1.11-1.01 (4H, m), 1.00-0.78 (9H, m), 0.75-0.66 (3H, m).

[2] Mass spectrometry by MALDI-TOF-MS: m/z=603.415 (M−H)$^-$

Example 8

Production of Compound (29)

Compound (29) was produced as in Example 1 except that amine compound (29) and pyridone compound (29) were respectively used in place of amine compound (1) and pyridone compound (1) in Example 1.

[Chem. 16]

-continued

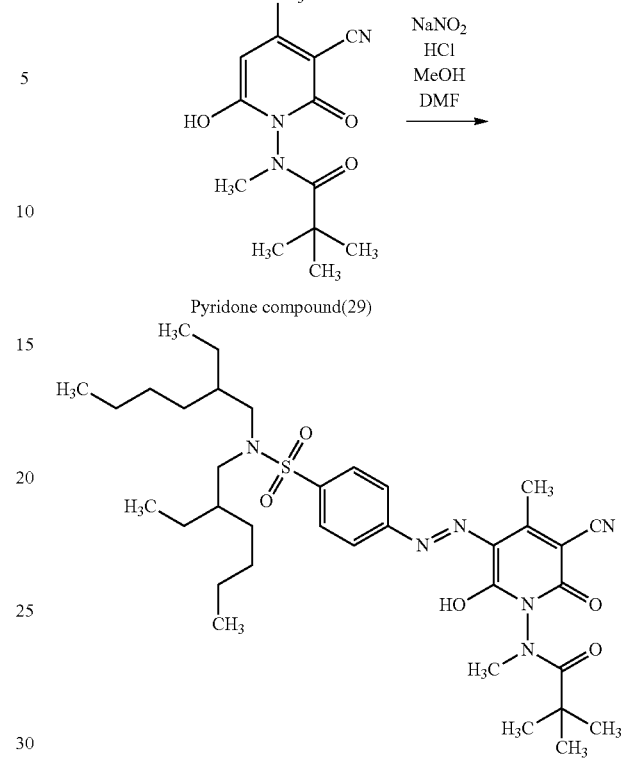

Pyridone compound(29)

Compound(29)

Analytical Results of Compound (29)

[1] $^1$H-NMR (CDCl$_3$) δ (ppm): 14.62 (1H, s), 7.88 (2H, d, J=8.77 Hz), 7.54 (2H, d, J=8.77 Hz), 3.52 (3H, s), 3.04-2.92 (4H, m), 2.66 (3H, s), 1.41 (9H, s), 1.31-1.06 (17H, m), 0.91-0.81 (13H, m).

[2] Mass spectrometry by MALDI-TOF-MS: m/z=669.776 (M−H)$^-$

Example 9

Production of Compound (30)

Compound (30) was produced as in Example 1 except that amine compound (30) and pyridone compound (30) were respectively used in place of amine compound (1) and pyridone compound (1) in Example 1.

[Chem. 17]

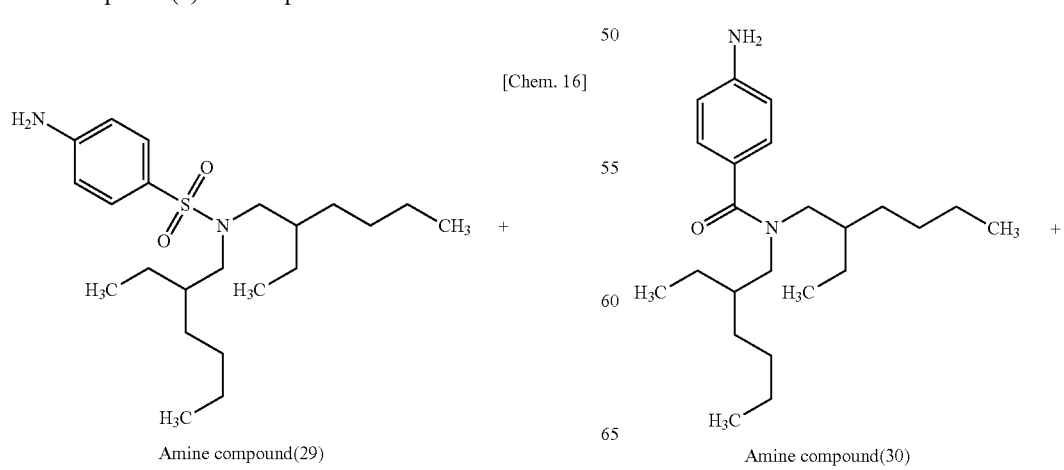

Amine compound(29)

Amine compound(30)

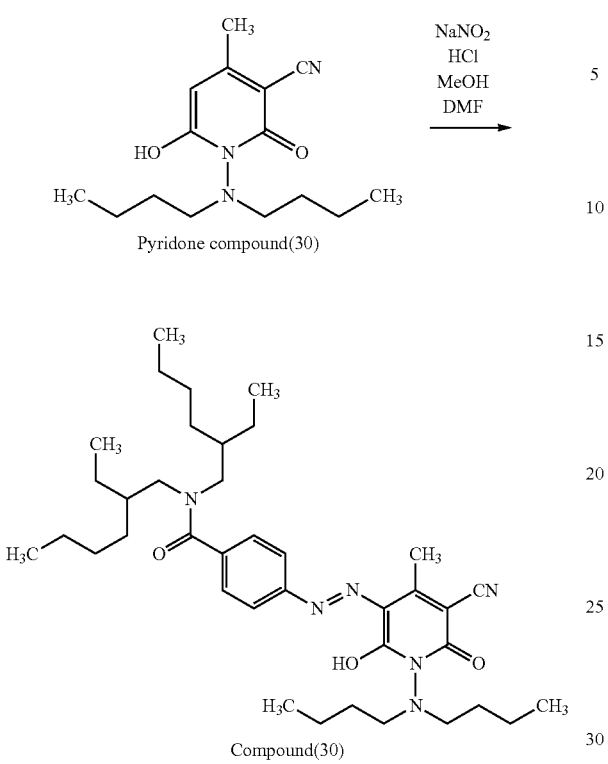

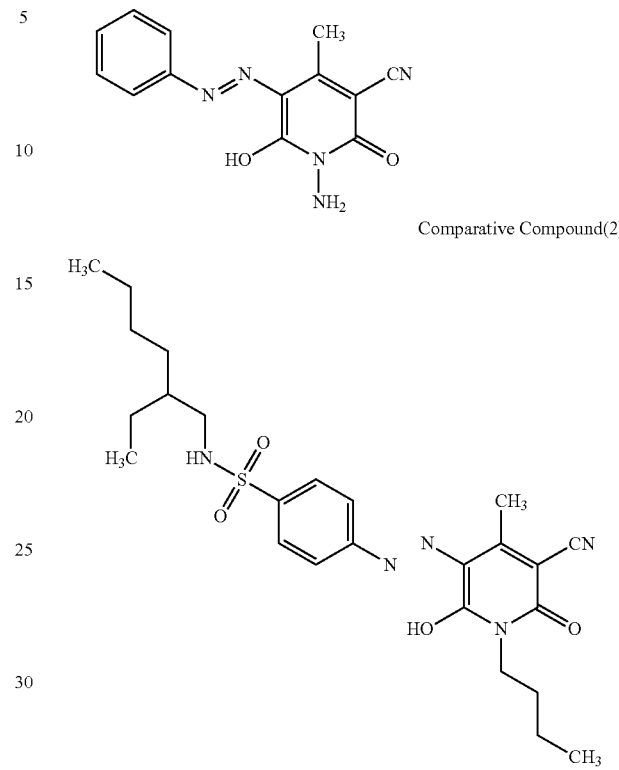

Analytical Results of Compound (30)

[1] $^1$H-NMR (CDCl$_3$) δ (ppm): 15.02 (1H, s), 7.49 (4H, d, J=2.54 Hz), 3.50-3.38 (2H, m), 3.37-3.26 (2H, m), 3.20-3.09 (4H, m), 2.63 (3H, s), 1.64 (2H, s), 1.60-1.47 (1H, br), 1.45-1.02 (23H, m), 0.99-0.76 (15H, m), 0.74-0.61 (3H, m).

[2] Mass spectrometry by MALDI-TOF-MS: m/z=647.401 (M−H)$^-$

Production of Ink

Inks of the present invention and Comparative Inks were produced by the process described below.

Production Example of Ink (1)

Ink (1) of the present invention was prepared by mixing 5 parts of Compound (1) as the water-insoluble coloring compound of the present invention, 350 parts of toluene, 350 parts of ethyl acetate, and 300 parts of 2-butanone.

Production Examples of Inks (2), (4), (8), (13), (15), (23), (28), (29), and (30)

Inks (2), (4), (8), (13), (15), (23), (28), (29), and (30) were prepared as in Production Example of Ink (1) except that Compounds (2), (4), (8), (13), (15), (23), (28), (29), and (30) were respectively used as the water-insoluble coloring compound in place of Compound (1) in Production Example of Ink (1).

Production Examples of Comparative Inks (1) and (2)

Comparative Inks (1) and (2) were prepared as in Production Example of Ink (1) except that Comparative Compounds (1) and (2) shown below were respectively used as the water-insoluble coloring compound in place of Compound (1) in Production Example of Ink (1).

Evaluation

Production of Samples

Inks (1), (2), (4), (8), (13), (15), (23), (28), (29), and (30) and Comparative Inks (1) and (2) were each applied onto paper for contrast ratio measurement by bar coating (Bar No. 10) and were air-dried overnight to produce image samples. Chromaticity values (L*, a*, b*) in the L*a*b* color system of each image sample were measured with a reflection densitometer SpectroLino (manufactured by Gretag Macbeth AG).

Light Resistance Evaluation of Compound

Each of the image samples produced in the chromaticity measurement was charged in a xenon tester (Atlas Ci4000, manufactured by Suga Test Instruments Co., Ltd.) and was subjected to exposure conditions (irradiance: 0.39 W/m$^2$ at 340 nm, temperature: 40° C., relative humidity: 60%) for 10 hours. The reflection densities of printed matters were measured before and after the test. The color difference (ΔE) was calculated from the initial chromaticity values $a_0^*$, $b_0^*$, $L_0^*$ and the chromaticity values a*, b*, L after the exposure by the following expression:

$$\Delta E = \sqrt{(a^*-a_0^*)^2+(b^*-b_0^*)^2+(L^*-L_0^*)^2} \qquad \text{[Math. 1]}$$

The evaluation criteria are as follows:

A: ΔE<3.50

B: 3.50≤ΔE<5.00

C: 5.00≤ΔE

The evaluation results of Examples and Comparative Examples are summarized in Table 1.

TABLE 1

|  | Compound | Light resistance ΔE |
|---|---|---|
| Example 1 | Compound (1) | 3.64/B |
| Example 2 | Compound (4) | 1.70/A |
| Example 3 | Compound (8) | 2.81/A |
| Example 4 | Compound (13) | 3.98/B |
| Example 5 | Compound (15) | 4.32/B |
| Example 6 | Compound (23) | 2.37/A |
| Example 7 | Compound (28) | 1.64/A |
| Example 8 | Compound (29) | 3.77/B |
| Example 9 | Compound (30) | 2.44/A |
| Comparative Example 1 | Comparative Compound (1) | 10.6/C |
| Comparative Example 2 | Comparative Compound (2) | 5.20/C |

As obvious from Table 1, the water-insoluble coloring compound of the present invention has excellent light resistance.

Production of Yellow Color Filter Resist Composition

Example 11

Ink (11) of the present invention was prepared by mixing 12 parts of Compound (1) as the water-insoluble coloring compound of the present invention and 120 parts of cyclohexanone and dispersing the mixture with an attritor (manufactured by Mitsui Mining Co., Ltd.) for 1 hour.

Twenty-two parts of Ink (11) was slowly added to a solution of 6.7 parts of an acrylic copolymer composition (weight average molecular weight Mw: 10000) composed of, as a monomer ratio, 40% by mass of n-butyl methacrylate, 30% by mass of acrylic acid, and 30% by mass of hydroxyethyl methacrylate, 1.3 parts of dipentaerythritol pentaacrylate, and 0.4 parts of 2-benzyl-2-dimethylamino-1-(4-morpholinophenyl)-butanone (photopolymerization initiator) in 96 parts of cyclohexanone, followed by stirring at room temperature for 3 hours. The reaction solution was filtered through a filter of 1.5 μm pore size to yield color filter yellow resist composition (1) of the present invention.

Color filter yellow resist composition (1) was spin-coated on a glass substrate and was then dried at 90° C. for 3 min, and the entire surface was then exposed to light and post-cured at 180° C. to produce color filter (1).

Examples 12 and 13

Color filter yellow resist compositions (8) and (15) were prepared as in Example 11 except that compounds (8) and (15) were respectively used in place of Compound (1) as the water-insoluble coloring compound in Example 11. Furthermore, color filters (8) and (15) were produced as in Example 11 except that the resulting color filter yellow resist compositions (8) and (15) were respectively used in place of color filter yellow resist composition (1).

Comparative Examples 3 and 4

Comparative color filter yellow resist compositions (1) and (2) were prepared as in Example 11 except that Comparative Compounds (1) and (2) were respectively used in place of Compound (1) in Example 11. Furthermore, comparative color filters (1) and (2) were produced as in Example 11 except that the resulting comparative color filter yellow resist compositions (1) and (2) were respectively used in place of color filter yellow resist composition (1).

Preparation of Thermal Transfer Recording Sheet

Example 14

Ink (14) of the present invention was prepared by gradually adding 5 parts of a polyvinyl butyral resin (Denka 3000-K, manufactured by Denki Kagaku Kogyo K.K.) to a solution of 13.5 parts of Compound (4), as the water-insoluble coloring compound of the present invention, in a mixture of 45 parts of methyl ethyl ketone and 45 parts of toluene with stirring.

Ink (14) was applied onto a polyethylene terephthalate film (Lumirror, manufactured by Toray Industries, Inc.) having a thickness of 4.5 μm so as to have a dried thickness of 1 μm and was dried to produce thermal transfer recording sheet (4).

Examples 15 to 19

Thermal transfer recording sheets (13), (23), (28), (29), and (30) were produced as in Example 14 except that Compounds (13), (23), (28), (29), and (30) were respectively used in place of Compound (4) as the water-insoluble coloring compound in Example 14.

Comparative Examples 5 and 6

Comparative thermal transfer recording sheets (1) and (2) were produced as in Example 14 except that Comparative Compounds (1) and (2) were respectively used in place of Compound (4) as the water-insoluble coloring compound in Example 14.

Evaluation of Light Resistance

Each of the resulting color filters and the thermal transfer recording sheets was charged in a xenon tester (Atlas Ci4000, manufactured by Suga Test Instruments Co., Ltd.) and was subjected to exposure conditions (irradiance: 0.39 W/m² at 340 nm, temperature: 40° C., relative humidity: 60%) for 50 hours. The reflection densities of printed matters were measured before and after the test. The color difference (ΔE) was calculated from the initial chromaticity values $a_0^*$, $b_0^*$, $L_0^*$ and the chromaticity values a*, b*, L* after the exposure by the following expression:

$$\Delta E = \sqrt{(a^*-a_0^*)^2+(b^*-b_0^*)^2+(L^*-L_0^*)^2} \quad [\text{Math. 2}]$$

The evaluation criteria are as follows:
A: ΔE<3.50
B: 3.50≤ΔE<5.00
C: 5.00≤ΔE

The results are shown in Table 2.

TABLE 2

|  | Compound | Application | Light resistance ΔE |
|---|---|---|---|
| Example 11 | Compound (1) | Color filter (1) | 2.99/A |
| Example 12 | Compound (8) | Color filter (8) | 2.68/A |
| Example 13 | Compound (15) | Color filter (15) | 4.21/B |
| Example 14 | Compound (4) | Thermal transfer recording sheet (4) | 2.76/A |
| Example 15 | Compound (13) | Thermal transfer recording sheet (13) | 3.37/A |
| Example 16 | Compound (23) | Thermal transfer recording sheet (23) | 2.54/A |
| Example 17 | Compound (28) | Thermal transfer recording sheet (28) | 2.32/A |
| Example 18 | Compound (29) | Thermal transfer recording sheet (29) | 2.56/A |
| Example 19 | Compound (30) | Thermal transfer recording sheet (30) | 4.89/B |

TABLE 2-continued

| | Compound | Application | Light resistance ΔE |
|---|---|---|---|
| Comparative Example 3 | Comparative Compound (1) | Color filter (1) | 12.8/C |
| Comparative Example 4 | Comparative Compound (2) | Color filter (2) | 6.87/C |
| Comparative Example 5 | Comparative Compound (1) | Thermal transfer recording sheet (1) | 15.1/C |
| Comparative Example 6 | Comparative Compound (2) | Thermal transfer recording sheet (2) | 7.76/C |

As obvious from Table 2, the color filters and the thermal transfer recoding sheets containing the water-insoluble coloring compound of the present invention have excellent light resistance.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-010325, filed Jan. 20, 2012, which is hereby incorporated by reference herein in its entirety.

The invention claimed is:

1. A water-insoluble coloring compound having a structure represented by Formula (1):

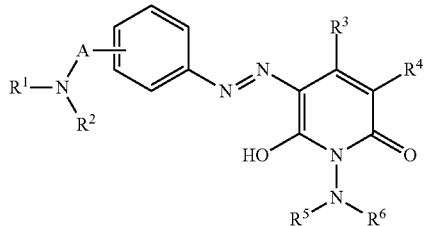

Formula (1)

in Formula (1), both $R^1$ and $R^2$ represent a 2-ethylehexyl group; $R^3$ represents an alkyl group, an aryl group, or an amino group; $R^4$ represents a hydrogen atom, a cyano group, a carbamoyl group, a carboxylic acid ester group, or a carboxylic acid amide group; $R^5$ and $R^6$ each independently represent a hydrogen atom, an alkyl group, or an acyl group or $R^5$ and $R^6$ bind to each other to form a ring; and A represents a carbonyl group.

2. The water-insoluble coloring compound according to claim 1, wherein in Formula (1), $R^4$ represents a cyano group.

3. An ink comprising the water-insoluble coloring compound according to claim 1.

4. A thermal transfer recording sheet comprising
   a base material and
   a coloring material layer formed on the base material from a composition containing the water-insoluble coloring compound according to claim 1.

5. A color filter resist composition comprising the water-insoluble coloring compound according to claim 1.

* * * * *